United States Patent
Kim et al.

(10) Patent No.: US 7,259,010 B2
(45) Date of Patent: Aug. 21, 2007

(54) EXPRESSION VECTOR FOR ANIMAL CELL CONTAINING NUCLEAR MATRIX ATTACHMENT REGION OF INTERFERON BETA

(75) Inventors: Jeong Do Kim, Yongin (KR); Hye-Yeon Hwang, Kunpo (KR); Dong-jun Kim, Suwon (KR); Kwanghee Baek, Seoul (KR); Yeup Yoon, Kwacheon (KR); Jaeseung Yoon, Yongin (KR); Alex Inkeun Leesong, Strathfield (AU)

(73) Assignee: Pangen Biotech Inc. (KR)

( * ) Notice: Subject to any disclaimer, the term of this patent is extended or adjusted under 35 U.S.C. 154(b) by 215 days.

(21) Appl. No.: 10/450,556

(22) PCT Filed: Dec. 14, 2001

(86) PCT No.: PCT/KR01/02178

§ 371 (c)(1),
(2), (4) Date: Nov. 10, 2003

(87) PCT Pub. No.: WO02/48379

PCT Pub. Date: Jun. 20, 2002

(65) Prior Publication Data

US 2004/0072352 A1    Apr. 15, 2004

(30) Foreign Application Priority Data

Dec. 15, 2000 (KR) ............................... 2000-77279
Dec. 14, 2001 (KR) ............................... 2001-79227

(51) Int. Cl.
*C12N 15/63* (2006.01)
(52) U.S. Cl. .................................. 435/320.1; 536/24.1
(58) Field of Classification Search ..................... None
See application file for complete search history.

(56) References Cited

OTHER PUBLICATIONS

Lucas et al. High-level production of recombinant proteins in CHO cells using a dicistronic DHFR intron expression vector. Nucleic Acids Res. May 1, 1996;24(9):1774-9.*
"A glimpse of Chromosomal order", S.M. Gasser, et al., 1987 Elsevier Science Publishers.B.V. Trends Genet 3:16-22.
"Introduction of Purified Genes Into Mammalian Cells", R. Kucherlapati, et al, CRC Critical Reviews in Biochemistry 16:349-379, 1984.
"Germ-Line Transformation of Mice", R. Palmiter, et al., 1986 Annual Reviews Inc. Annual Rev. Genet. 20:465-499.
"Boundary functions in the control of gene expression", J.C. Eissenberg, et al., TIG Oct., vol. 7, No. 10 335-340, 1991.
"Matrix-attachment regions can impart position-independent regulation of a tissue-specific gene in transgenic mice", R. MCKnight, et al., Proc. Natl. Acad. Sci. USA vol. 89, pp. 6943-6947, 1992.
"Potition-Independent Transgene Expression Mediated by Boundary Elements from the Apolipoprotein B Chromatin Domain", M. Kalos, et al., Molecular and Cellular Biology, Jan. 1995, p. 198-207.
"Scaffold-Attached Regions from the Human Interferon B Domain Can Be Used To Enhance the Stable Expression of Genes under the Control of VArious Promoters", D. Klehr, et al., 1991 American Chemical Society Biochem. 5:1264-1270.
"Dissection of the Ability of the Chicken Lysozyme Gene 5' Matrix Attachment Region To Stimulate Transgene Expression and To Dampen Position Effects", L. Phi-Van, et al., 1996 American Chemical Society Biochem. 35:10735-10742.
Kraevskii, V.A., et al, "Stable bent and low-melting DNA sequences in the region of the replication origin of chicken alpha-globin gene domain", Mol., Biol. 26 672-678, 1992.
"Anchorage of the Chinese Hamster Dihydrofolate Reductase Gene to the Nuclear Scaffold Occurs in an Intragenic REgion", E. Kas, et al, 1987 Academic Press Limited J Mol Biol 198:677-692.
"Yeast ARS function and nuclear matrix association coincide in a short sequence from the human HPRT Locus", R. Sykes, et al, Mol Gen Genet (1988) 212:301-309.
A-T-rich scaffold attachment regions flank the hematopoietic serine protease genes clustered on chromosome 14q11.2., Hanson RD, Ley TJ, 81md (1992 79:610-8 Abstract Only.
"Hierarchical Binding of DNA Fragments Derived from Scaffold-Attached Regions: Correlation of Properties in Vitro and Functions in Vivo", C. Mielke, 1990 American Chemical Society.
"Scaffold Attachment Region-Mediated Enhancement of Retroviral Vector Expression in Primary T Cells", M. Agarwal, et al., Journal of Virology, May 1998, p. 3720-3728.
"Human Beta Interferon Scaffold Attachment Region Inhibits De Novo Methylation and Confers Long-Term, Copy Number-Dependent Expression to a Retroviral Vector", Dang et al., Journal of Virology, Mar. 2000, p. 2671-2678.
"Effects of Scaffold Attachment Region on the Transgene Expression in Retrovirus Vector-Tranduced Primary T Cells and Macrophages", J. Auten, et al, Human Gene Therapy May 20, 1999, 1389-1399.
"Identification of the proteins responsible for SAR DNA binding in nuclear matrix of Cucurbita pepo.", R. Markiewecz, et al., Acta Biochem Pol. (1995) 42:171-6 Abstract Only.

* cited by examiner

*Primary Examiner*—Daniel M. Sullivan
(74) *Attorney, Agent, or Firm*—Blakely Sokoloff Taylor & Zafman

(57) ABSTRACT

The present invention relates to mammalian expression vectors including nuclear matrix attachment region of human interferon β, and more particularly to pPGM-1, pPGM-2 and pPGM-3 including nuclear matrix attachment region of interferon β gene. Those expression vectors confer position independent expression of the introduced foreign gene, thus increasing the frequency of colonies which efficiently express the recombinant protein.

5 Claims, 11 Drawing Sheets pSVβ          pSVβ /I

AAGCTTG CTAGCGGCCG CAGATCTGTT AACTCGAG
|   | | | |
HindIII NheI NotI XhoI

5'...TAATA CGACT CACTA TAGGG AGACC CAAGC TGGCT AGCGT T TAAA CTTAA GCTTG
         T7 Promoter                       Nhe I     Pme I    Afl II GTACC GAGCT CGGAT CCACT AGTCC AGTGT GGTGG AATTC TGCAG A TATC CAGCA
               BamH I          BstX I              EcoR V CAGTG GCGGC CGCTC GAGTC TAGAG GGCCC GTTTA AACAC GCGT... 3'
 BstX I    Not I    Xho I    Xba I    Apa I    Pme I    Mlu I GCTAGCGGC CGCAGATCTG TTAACTCGAG
*Nhe*I
*Not*I
*Xho*I

EXPRESSION VECTOR FOR ANIMAL CELL CONTAINING NUCLEAR MATRIX ATTACHMENT REGION OF INTERFERON BETA

The present patent application is a non-provisional application of International Application No. PCT/KR01/02178, filed Dec. 14, 2001.

BACKGROUND OF THE INVENTION (a) Field of the Invention

The present invention relates to mammalian expression vectors including a nuclear matrix attachment region of interferon β gene, and more particularly to pPGM-1, pPGM-2, and pPGM-3.

(b) Description of the Related Art

Various expression systems including microorganisms, plants, yeasts, insect cells, mammalian cells, etc. have been used to express and obtain target proteins in large quantities to apply to medical and industrial uses. Microorganisms are the easiest systems to use, and microorganism expression systems suitable for various applications have been developed and are commonly used.

However, microorganism expression systems have some limitations. The most serious limitation is that since protein expression and modification mechanisms (glycosylation, phosphorylation, amidation) of microorganisms differ from those of mammalian cells, even if the same gene is expressed in a microorganism system, the structure or characteristics of expressed proteins is not completely identical to the original protein. Therefore, production of recombinant proteins using microorganism expression systems frequently expresses proteins that are inactivated because modification does not occur after synthesis, or that partially differ in modification or structure even if they are not significantly different in function. In addition, the recombinant protein production process using microorganism expression systems should be accompanied by additional contaminant removal due to contamination of microorganisms, contamination of microorganism endotoxin, etc.

Meanwhile, mammalian expression systems, although they are the most suitable systems for expressing mammalian proteins, have not been easily industrialized because recombinant protein expression efficiency is low and thus the unit cost of production is high, and the mammalian cell handling process is difficult. Presently used industrial mammalian cell lines include CHO (Chinese Hamster Ovary), BHK (Baby Hamster Kidney), myeloma, etc., and an expression vector including the gene of interest is transfected into the mammalian cell line to express aimed foreign proteins.

Mammalian cells maintain various protein modification mechanisms including glycosylation, and protein obtainment and purification processes are easier when proteins are secreted to a culture medium. Most mammalian cells require complex additives such as serum protein, etc. in the culture process, while CHO cells can be cultured in a medium without serum and protein, rendering it the most suitable host for expression of recombinant proteins. In addition, characteristics of CHO cells are well known due to their having been used in many studies, and they have advantages of a high growth rate and that mass suspension culture is possible.

Generally, in order to express a transgene in a mammalian cell, a vector having a selection marker and a transgene are simultaneously transfected. Transfected cells are cultured and selected in a selection medium. However, expression frequency thereof is very low. One of the reasons is that these transgenes should be integrated in chromosomes of a host cell in mammalian cells contrary to the microorganism system. Additionally, even if stable transfectants are selected, the expression amount is difficult to predict. This is because gene integration positions differ according to cells, and expression aspects differ according to integration positions. Therefore, the copy number of transgenes in mammalian cells and the gene expression amount do not have an explicit correlation therebetween (Grindley et al., 1987, Trends Genet. 3, 16-22; Kucherlapati et al., 1984, Crit. Rev. Biochem. 16, 349-381; Palmiter et al., 1986, Annu. Rev. Genet. 20, 465-400). Gene expression in mammalian cells is mostly repressed by a nucleic acid base near the integration position, and thus stably integrated transgenes would often be expressed in a very low level (Eissenberg et al., 1991, Trends Genet. 7., 335-340; Palmiter et al., 1986, Annu. Rev. Genet. 20, 465-499).

Usability of nucleic acid factors for protecting transgene expression from position effects has been reported in many systems. As the nucleic acid factors, an insulator factor and a nuclear matrix attachment region (MAR) or scaffold attachment region (SAR), etc. can be used. Although operation mechanisms thereof have not been clarified, when included in transgene constructs, they induce position independent gene expression and the expression amount is determined by the copy number of gene (McKnight, R. A. et al., 1992, Proc. Natl. Acad. US. 89, 6943-6947).

Kalos et al. have combined the MAR factor of the human apolipoprotein B gene with a minimal promoter transgene construct and induced gene expression in mammalian cells to increase expression of the transcript by about 200 times (Kalos et al., 1995, Mol. Cell. Biol. 15, 198-207). Similarly, it has been reported that the MAR factor of the chicken lysozyme A gene and the SAR factor of human interferon β, etc. confer position-independent transgene expression in vertebrates (Eissenberg et al., 1991, Trends Genet. 7, 335-340; Klehr et al., 1991, Biochemistry 30, 1264-1270). However, no attempt to apply the MAR/SAR factor to substantially increase protein production in CHO cell lines has been reported, nor has industrial profit been identified.

SUMMARY OF THE INVENTION

Accordingly, it is an object of the present invention to provide a vector which confers increased foreign protein expression efficiency in mammalian cells.

It is another object of the present invention to provide a vector for position independent expression of foreign proteins.

It is still another object of the present invention to provide a vector comprising a nuclear matrix attachment region of interferon β gene for increasing the frequency of foreign protein expression and the amount of foreign protein expressed in mammalian cells.

It is further object of the present invention to provide a vector comprising multiple cloning sites to facilitate the cloning of transgenes.

It is still further object of the present invention to provide a vector capable of expressing foreign proteins in mammalian cells.

In order to achieve these objects, the present invention provides mammalian expression vectors comprising a nuclear matrix attachment region of interferon β gene, a promoter, and a transcription terminator.

The present invention also provides mammalian cells transfected with the expression vectors in which target genes are introduced.

The present invention also provides a method for production of proteins comprising the steps of introducing transgenes into mammalian expression vectors and introducing the vector into mammalian cells to express proteins from the transgenes.

DETAILED DESCRIPTION AND THE PREFERRED EMBODIMENTS

The present inventors invented optimum expression vectors for overcoming position-specific expression inhibition effect (hereinafter referred to as "position effect") and improving gene expression amounts in transgene expression in mammalian expression systems.

The mammalian expression vector of the present invention further added a useful base sequence to the existing expression vectors. The useful base sequence protects transgene expression from position effects of the host cell chromosome, and increases transgene expression in CHO (Chinese hamster ovary) or BHK (Baby hamster kidney) cells, etc., commonly used as commercial mammalian cells. The useful base sequence is preferably the nuclear matrix attachment region (MAR) or saffold attachment region (SAR).

The MAR/SAR factor is preferably selected from a group consisting of chicken lysozyme 5' MAR (Phi-Van, L. and Stratling, W. H., 1996, *Biochemistry* 35, 10735-10742, Gene bank #: X98408), chicken phi α globin 5'MAR (Kraevskii, V. A. et al., 1992, *Mol. Biol.* 26, 672-678, Gene bank #: X64113), CHO DHFR intron MAR (Kas, E. and Chasin, L. A., 1987, *J. Mol. Biol.* 198, 677-692, Gene bank #: X06654), human HRRT intron MAR (Sykes, R. C. et al., 1988, *Mol. Gen. Genet.* 212, 301-309, Gene bank #: X07690), human CSP-B gene flanking SAR (Hanson, R. D. and Ley, T. J., Gene bank #: M62716), and human interferon β gene flanking SAR (Mielke, C. et al., 1990, *Biochemistry* 29, 7475-7485, Gene bank #: M83137).

Influences of the MAR/SAR factor on transgene expression were analyzed by integrating 6 kinds of MAR/SAR factors into pSV-β-gal/ver I or pSV-β-gal/ver II and examining expression aspects of β-gal genes.

Six kinds of MAR/SAR factors were respectively integrated into upstream of a promoter of pSV-β-gal/ver I or pSV-β-gal/ver II to complete a test vector. The test vector was introduced to CHO DG44 cells to prepare a transfected cell line, and β-gal expression frequency and expression amount were measured.

The recombinant vector pSBβ/I including interferon β MAR factor was compared with pSV-β-gal as a control. The number of colonies increased by about 3 times in a G418 medium, and frequency of positive cell lines expressing β-gal increased to 71% compared to 35% of the control, thus the number of positive cell lines increased by 6 times.

Figure 3:
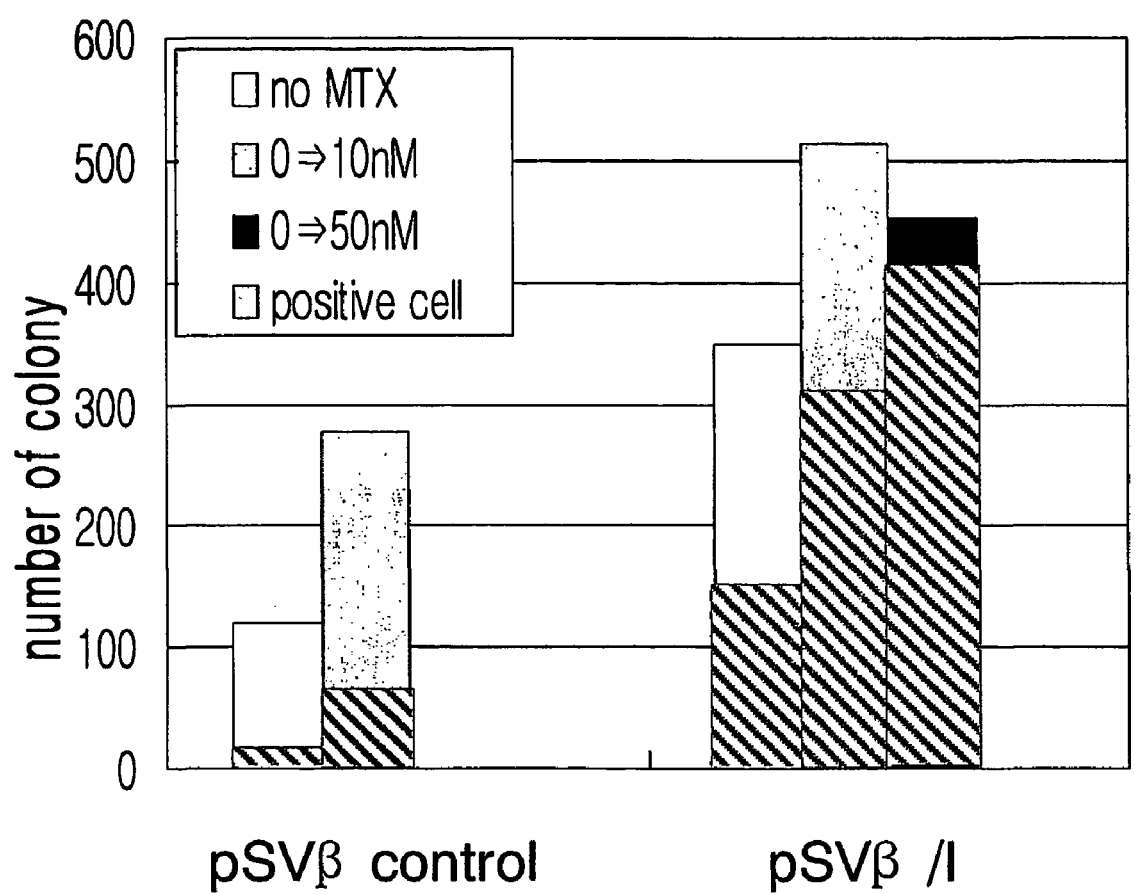
FIG. 3 shows frequency of positive cell lines that express β-gal when amplifying introduced genes by adding MTX

In addition, when pSVβ/I transfected cell lines were selected in a DHFR selection medium, the number of positive colonies that were produced in initial selection medium not including nucleoside increased by 10 times. When MTX was added to a culture medium to induce transgene amplification, the β-gal positive colony rate of the pSVβ/I transfected cell line was 90% or more of total colonies, and the number of positive cells increased to about 7 times as much as the control PSV-β-gal (FIG. 3).

Accordingly, the interferon β MAR factor of the present invention increases expression efficiency of transgenes and selection marker genes to largely enhance growth of transfected cell lines in selection medium, and shortens periods required for selecting transfected cell lines in selection mediums.

The present invention also provides mammalian expression vectors including a nuclear matrix attachment region of interferon β at a upstream of promoter 5'. The mammalian expression vectors are preferably pPGM-1, pPGM-2, and pPGM-3. The promoter is preferably selected from a group consisting of SV40 promoter, CMV (cytomegalovirus) promoter, and MMTV (Mouse Mammary Tumor Virus) promoter.

The pPGM-1 vector contains a 5409 bp including a nuclear matrix attachment region of the human interferon β gene, a SV40 virus promoter, and multiple cloning sites (MCS), and it can express various genes by integrating transgenes in multiple cloning sites. Multiple cloning sites include HindIII, NheI, NotI, and XhoI restriction sites. The base sequence of the pPGM-1 vector is listed as SEQ ID NO: 1 in the sequence listing program, and major factors included in the vector and their positions are shown in Table 1 and FIG. 7. The pPGM-1 vector was deposited with the Korean Culture Collection of Microorganisms under deposition no. KCCM 10232.

TABLE 1

| Sequence No. | Functions |
|---|---|
| 1–413 | Initial promoter and enhancer of SV40 virus |
| 414–448 | Multiple cloning sites (MCS) |
| 449–584 | Small T antigen of SV40 virus |
| 1194–2054 | β-lactamase: Amp$^R$ gene |
| 3225–5397 | Nuclear matrix attachment region of interferon β gene |

Figure 8:
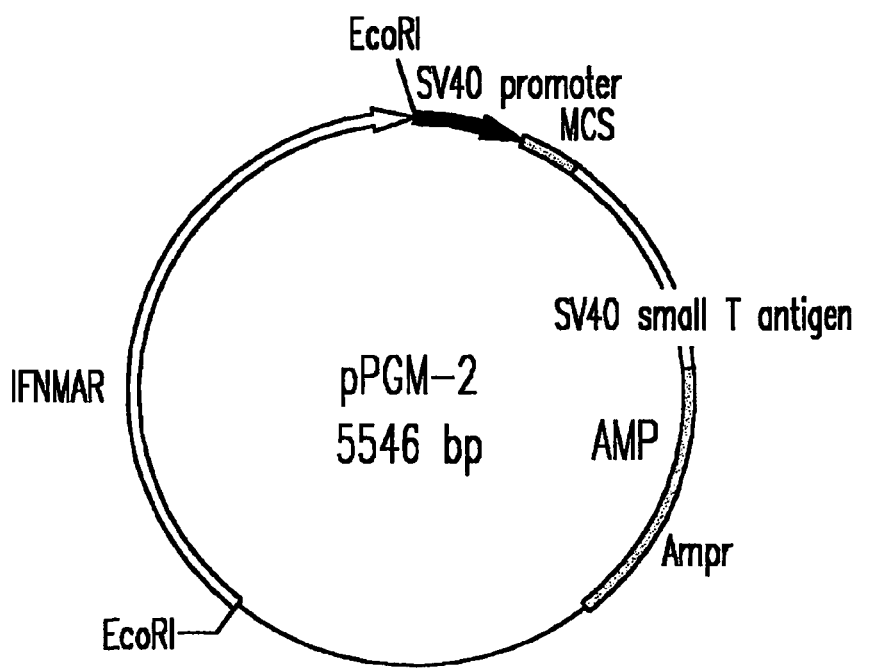
FIG. 8 shows the map of the pPGM-2 expression vector of the present invention and a base sequence of multiple cloning sites.

The pPGM-2 vector, which modifies multiple cloning sites of the pPGM-1 vector, includes a nuclear matrix attachment region of the interferon β gene, a SV40 promoter, and multiple cloning sites. The base sequence of the pPGM-2 is listed as SEQ ID NO: 2, and the structure of the vector is shown in FIG. 8 and Table 2. The multiple cloning sites of the pPGM-2 vector include NheI, PmeI, AflII, BamHI, BstXI, EcoRV, NotI, XhoI, XbaI, ApaI, PmeI, and MluI restriction sites. The pPGM-2 vector was deposited with the Korean Culture Collection of Microorganisms under deposition no. KCCM 10338.

TABLE 2

| Sequence No. | Functions |
| --- | --- |
| 1–413 | SV40 promoter |
| 426–445 | T7 promoter |
| 446–579 | Multiple cloning sites (MCS) |
| 1331–2191 | β-LACTAMASE: $Amp^R$ gene |
| 3361–5534 | Nuclear Matrix Attachment Region of interferon β gene |

Figure 9:
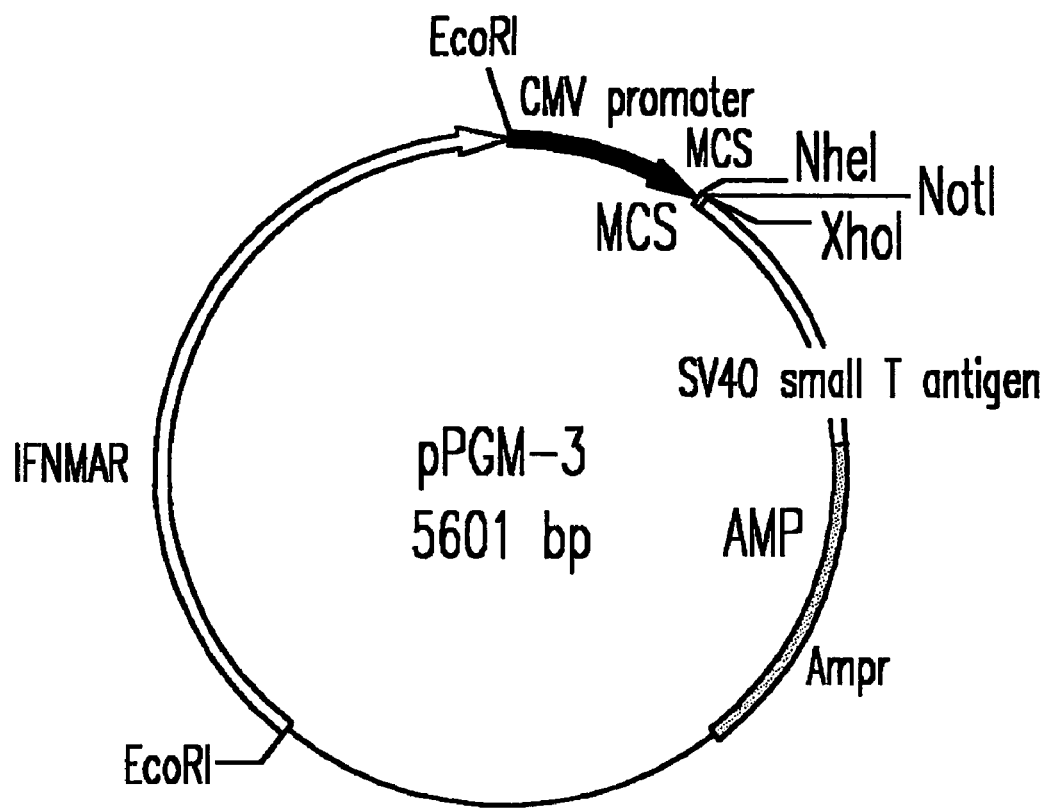
FIG. 9 shows the map of the pPGM-3 expression vector of the present invention.

The pPGM-3 vector which substitutes the SV40 promoter of the pPGM-1 vector with the CMV (Cytomegalovirus) derived promoter consists of 5601 bp. The base sequence thereof was shown as SEQ ID NO: 3, and the structure is shown in FIG. 9 and Table 3. The pPGM-3 vector was deposited with the Korean Culture Collection of Microorganisms under KCCM 10339.

TABLE 3

| Sequence No. | Functions |
| --- | --- |
| 1–611 | SV40 promoter |
| 612–640 | Multiple cloning sites (MCS) |
| 1396–2246 | β-lactamase: $Amp^R$ gene |
| 3417–5589 | Nuclear Matrix Attachment Region of interferon β gene |

The pPGM-1 vector, pPGM-2 vector, and pPGM-3 vector of the present invention are superior to common vectors in number of positive cells expressing transgenes, frequency, and expression amount. Therefore, the pPGM-1 vector, pPGM-2 vector, and pPGM-3 vector of the present invention can be used for expressing and producing transgenes in mammalian cells, and they can produce recombinant proteins such as enzyme and cytokine.

In addition, the present invention introduces a transgene into a vector including a nuclear matrix region of the interferon β gene, and introduces it into a mammalian cell to provide a transfected cell line. The transfected cell line is selected by culturing in a medium to which a selection marker or MTX is added. A transgene is a gene encoding all kinds of proteins capable of being expressed as recombinant proteins. Representative examples include insulin, cytokine (interleukin, tumor necrosis factor, interferon, colony stimulation factor, chemokine, etc.), erythropoietin, etc. The transfected cell line can be produced by a common method.

In addition, the present invention provides a method of producing proteins comprising: introducing a transgene into a vector including a nuclear matrix attachment region of the interferon β gene, and introducing the vector into a mammalian cell to express proteins from a transgene. The vector is preferably selected from a group consisting of pPGM-1 (KCCM 10232), pPGM-2(KCCM 10338), and pPGM-3 (KCCM 10339). The mammalian cell can be any mammalian-derived cell, and it is preferably CHO (Chinese hamster ovary).

As described above, the pPGM-1 vector, pPGM-2 vector, and pPGM-3 vector of the present invention improve repression of transgene expression caused by surrounding bases and increase expression. In addition, the expression vector of the present invention can be effectively applied to mass production of industrially useful proteins, and it can produce recombinant proteins having the same structure and functions as original proteins of higher animals.

The present invention will be explained in further detail with reference to the following Examples and Comparative Examples. However, these are to illustrate the present invention and the present invention is not limited to them.

EXAMPLE 1

Cloning of MAR or SAR Factor

Genomic DNA was isolated from human G-2 cells using a Wizard Genomic DNA purification kit (Promega, U.S.A.). 10 μg of DNA were cut with ClaI, SmaI, XbaI, and XhoI restriction enzymes to use in the PCR process. DNA to be used in PCR was separated and purified from a CHO chicken cell line and a chicken embryo by a similar method.

200 ng of the isolated genomic nucleic acid was used as a template, and 25 pmole of each primer, 0.5 mM of dNTP, and ExTaq polymerase (Takara Shuzo Co., Japan) were added to carry out PCR. The base sequence of primer used for each MAR/SAR factor and size of DNA fragment obtained by PCR are as shown in Table 4. PCR was carried out using a GeneAmp PCR system 9600 (Perkin-Elmer Corp. U.S.A.), and PCR conditions are as shown in Table 5.

TABLE 4

| MAR/SAR factor | Primer | SEQ ID NO: | Size |
| --- | --- | --- | --- |
| Chicken lysozyme 5'MAR | 5'-GGA TCC ATA ATA TAA CTG TA-3'<br>5'-AAG CTT AAA AGA TTG AAG CA-3' | 4<br>5 | 1668 bp |
| Chicken phi α globin 5'MAR | 5'-AAG CTT TTA ACC AAC AAA AA-3'<br>5'-CTG CAG ACC TAA CCT GTC AC-3' | 6<br>7 | 619 bp |
| CHO DHFR intron MAR | 5'-TAT ACG TGA ATA GTT TTT CT-3'<br>5'-GAG TTG GAA CTG AGA AGT TC-3' | 8<br>9 | 549 bp |
| Human HPRT intron MAR | 5'-AAG CTT GGT CAA GA TGG TG-3'<br>5'-GCT GGG CGT GGT GGT GCC TG-3' | 10<br>11 | 580 bp |
| Human CSP-8 gene SAR | 5'-GGA TCC GAT TCT CCT TGA TG-3'<br>5'-GAA TTC AAA CAA CTC AAT AG-3' | 12<br>13 | 1233 bp |

TABLE 4-continued

| MAR/SAR factor | Primer | SEQ ID NO: | Size |
|---|---|---|---|
| Human interferon β SAR | 5'-GAA TTC AGC AAG GTC GCC AC-3'<br>5'-TTG TAT CAA CTT TCT ACA AT-3' | 14<br>15 | 2174 bp |

TABLE 5

| Step | Conditions | Cycle |
|---|---|---|
| 1 | 94° C., 2 min | 1 |
| 2 | 94° C., 40 sec; 65° C., 40 sec; 72° C., 40 sec | 2–31 |
| 3 | 72° C., 10 min | 32 |

Fragments of chicken lysozyme 5' MAR (Gene bank #: X98408, hereinafter referred to as "lyso MAR"), chicken phi α globin 5' MAR (Gene bank #: X64113, hereinafter referred to as "phi-a MAR"), CHO DHFR intron MAR (Gene bank #: X06654, hereinafter referred to as "DHFR MAR"), human HPRT intron MAR (Gene bank #: X07690, hereinafter referred to as "HPRT MAR"), human CSP-B gene flaking SAR (Gene bank #: M62716, hereinafter referred to as "CSP-B MAR"), and human interferon β gene flanking SAR (Gene bank #: M83137, hereinafter referred to as "interferon β MAR") were separated by the above-explained method.

The PCR product was subcloned in pT7blue (R) (Novagene, U.S.A.) or a pCR 2.1 (Invitrogen, U.S.A.) vector. HPRT MAR, DHFR MAR, and lyso MAR were subcloned in a pT7blue (R) vector, and phi-a MAR, CSP-B MAR, and interferon β MAR were subcloned in PCR 2.1.

EXAMPLE 2

Construction of pSV-β-gal/ver I and pSV-β-gal/ver II Vectors

Figure 1:
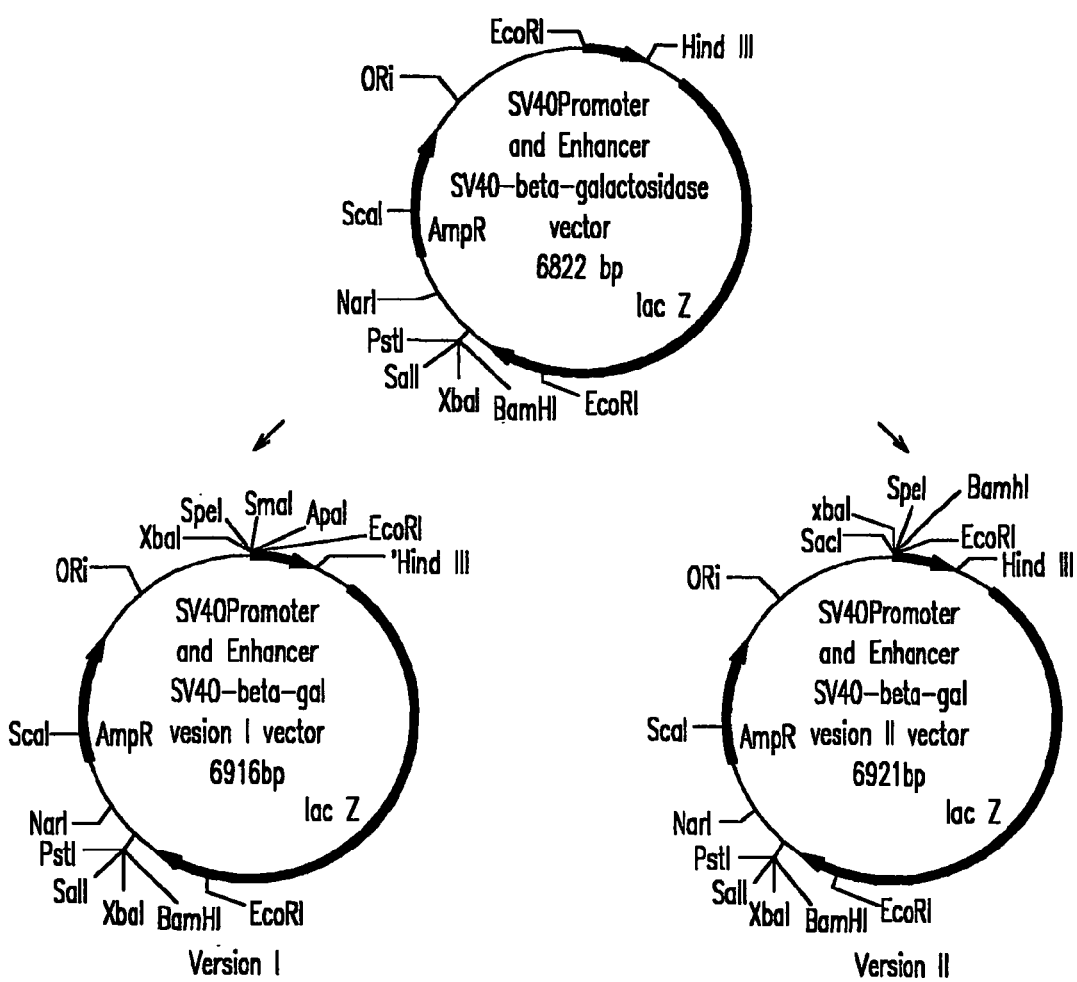
FIG. 1 shows a structure of a vector constructed by modifying a pSV-β-gal vector in order to construct the expression vector of the present invention.

In order to effectively clone multiple MAR/SAR factors subcloned in the pT7blue (R) or pCR 2.1 vector at upstream of a SV40 promoter of a pSV-β-gal (hereinafter referred to as 'pSVβ') vector, modified pSV-β-gal/ver I and PSV-β-gal/ver II vectors were constructed (FIG. 1).

(1) Construction of pSV-β-gal/ver I

PCR was carried out with pSVβ as a template with primers of SEQ ID NO: 16 and SEQ ID NO: 17 to obtain a fragment including the SV40 promoter. The fragment was cut with SpeI and HindIII enzymes, and a 443 bp of DNA fragment including SV40 was purified with a Geneclean III kit (Bio 101, U.S.A). It was subcloned in a opened pBluescript SK (+) vector (Stratagene, U.S.A.) with SpeI and HindIII enzymes to construct pBS/SV40 I.

The pBS/SV40 I was digested with ScaI and HindIII enzymes to separate a 1240 bp DNA fragment, and it was subcloned in pSVβ treated with the same enzymes to complete a pSV-β-gal/ver vector.

(2) Construction of pSB-β-gal/ver II Vector

A pSVβ was cut with EcoRI and HindIII to obtain a 420 bp fragment by the above-explained method, and the fragment was inserted into a pBluescript SK (+) vector opened with the same enzymes to construct a pSV-β-gal/ver II vector.

EXAMPLE 3

Construction of a Vector Including MAR Factor and β-gal Gene

MAR factors were separated from pT7blue(R)/HPRT MAR, bT7blue(R)/DHFR MAR, pT7blue(R)/lyso MAR, pCR 2.1/phi-a MAR, pCR 2.1/CSP-B MAR, and pCR 2.1/interferon β MAR, and cloned in pSVβ/I or pSVβ/II.

In a pSVβ/I, phi-a MAR and HPRT MAR (human HPRT intron MAR) were subcloned using SpeI/SmaI, and interferon β MAR and lyso MAR were subcloned using ApaI/SpeI. Constructed vectors were pSV-β-gal/phi-a MAR, pSV-β-gal/HPRT MAR, pSV-β-gal/interferon β MAR (hereinafter referred to as 'pSVβ/I'), and pSV-β-gal/lyso MAR.

Additionally, DHFR MAR and CSP-B MAR were subcloned in pSV-β-gal/ver II at BamHI/Xba I restriction site. Constructed vectors were pSV-β-gal/DHFR MAR and pSV-β-gal/CSP-B MAR respectively.

EXAMPLE 4

Construction of pCMVβ and pCMVβ/I

A SpeI-XhoI fragment including a MAR factor was deleted from a pSVβ/I vector and the vector was self-ligated. After cleavage by ApaI and HindIII, a CMV promoter fragment was inserted to construct a pCMVβ vector. The CMV promoter was amplified by PCR with primers of SEQ ID NO: 18 and SEQ ID NO:19 in a pcDNA3.1 vector. The sequences of SEQ ID NO: 18 and SEQ ID NO:19 include a ApaI or HindIII restriction site.

Also, a pSVβ I vector was digested with ApaI and HindIII restriction enzymes and a CMV promoter fragment was integrated therein to construct a pCMVβ/I vector.

Namely, pCMVβ is a vector without the MAR factor, and pCMVβ/I is a vector having the MAR factor.

EXAMPLE 5

Measurement of Gene Expression of pSVβ and pSVβ/I (1) Transfection

A CHO cell line DG44 deficient of the DHFR gene was cultured in a MEM-α medium (α-Minimum Essential Medium, Gibco BRL) to which 10% serum (fetal bovine serum) was added. $2 \times 10^5$ cells were inoculated on a 60 mm plate together with 3 ml of medium and cultured in 5% $CO_2$ incubator at 37° C. overnight, until transfection occurred.

Transfection was carried out by a liposome method. A pSV2Neo or pDCH1P vector having selection maker gene was co-transfected with each test vector in a mole ratio of 100:1, and a pSVβ vector was used as a control to perform the same experiment. 2 μg of each vector were mixed with lipid surfactant, DOSPER (BOEHRINGER Mannheim, German) and serum-free MEM-α medium and reacted at room temperature for 45 minutes, it was added to a rinsed cell together with a medium to culture for 5 hours, and then the reaction liquid was removed. Culture was carried out in MEM-α medium including 10% FBS and G418 (500 μg/ml) for 2 weeks in order to select the transfected cell line using a Neo gene, and culture was carried out in MEM-α medium not including a nucleoside for 2 weeks in order to select a DHFR gene, and β-gal expression was analyzed.

(2) Measurement of Frequency of β-gal Expression Positive Cell Line

Positive cells expressing β-gal were selected.

Cells cultured on a 100 mm plate were treated with a fixing agent (2% formaldehyde and 0.2% glutaraldehyde) at 4° C. for 10 minutes. They were washed with 1×PBS twice, and X-gal (1 mg/ml) was added to react them at 37° C.

A β-gal expression cell can be easily identified because it decomposes X-gal and shows a blue color. Positive cells were separated with a trypsin-EDTA solution, and the number of cells was measured with a hematocytometer.

Figure 2:
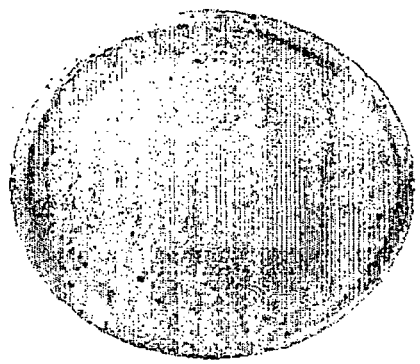
FIG. 2 shows the β-gal staining method which demonstrates the increase in the frequency of positive cells by nuclear matrix attachment region of interferon β gene.
Figure 2:
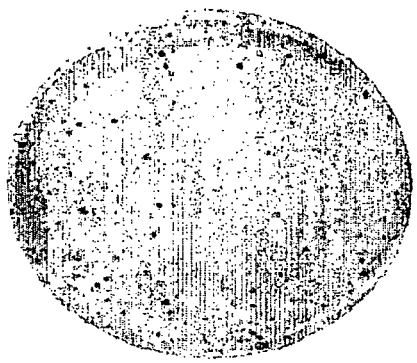
Figure 2:
Figure 2:

FIG. 2 is a photo of cells treated with X-gal after being transfected with pSVβ or pSVβ/I in order to identify β-gal expression cells. (a) shows cells transfected with pSVβ, and (b) shows cells transfected with pSVβ/I. A positive cell line showing a blue color of PSVβ/I transfected cell line is remarkable in the upper plate photo.

After transfection, the transfected cell line was selected using a Neo gene or a DHFR gene, and the number of positive cells expressing β-gal were measured.

Table 6 shows the number of β-gal positive cells of DG44/PSVβ or DG44/PSVβ/I selected using the Neo selection factor. Table 7 shows the number of β-gal positive cells of DG44/pSVβ or DG44/pSVβ/I selected using the DHFR selection factor.

TABLE 6

| | Total cell number | Positive Cell number | Negative Cell number | Positive Cell Frequency (%) |
|---|---|---|---|---|
| DG44/pSVβ | 222 | 145 | 77 | 34.68 |
| DG44/pSVβ/I | 659 | 191 | 468 | 71.02 |

TABLE 7

| | Total Cell number | Positive Cell number | Negative Cell number | Positive Cell Frequency (%) |
|---|---|---|---|---|
| DG44/pSVβ | 120 | 105 | 15 | 12.50 |
| DG44/pSVβ/I | 350 | 200 | 150 | 42.86 |

The total number of colonies and frequency of positive colonies increased, and the number of positive colonies remarkably increased, when the transfected cell lines were selected by culturing in selection maker existing media.

In addition, the transfected cell line (DG44/pSVβ, DG44/pSBβ/I) was adapted to a MTX-added medium to induce gene amplification. The β-gal expression frequency of the transfected cell line adapted to MTX 10 nM and 50 nM was measured. FIG. 3 is a graph measuring activity of the β-gal of MTX-adapted transfected cell line. 90% or more of the DG44/PSVβ/I transfected cell line selected in MTX expressed β-gal, and produced 7 times as many positive colonies as the control (pSVβ).

Accordingly, the interferon β MAR factor further enhanced expression activity of the SV40 promoter to increase frequency of positive cell lines by 6-10 times. A common transfected cell line preparation process requires that transfected cell lines should be selected from a selection medium for a very long period. However, it is expected that the MAR factor will sharply shorten the period of time required for development of transfected cell lines. In addition, the MAR factor affects expression of selected genes as well as target genes to largely enhance growth of recombinant cell lines in the selection medium.

(3) β-gal Activities of DG44/pSVβ and DG44/pSVβ/I

β-gal activity of the same cell as used to measure frequency of the β-gal expression positive cell line was measured.

A transfected cell line was cultured for 48 hours and washed with 1×PBS twice. 1 ml of STE (0.1M NaCl, 10 mM Tris-Cl (pH 8.0) and 1 mM EDTA (pH 8.0) solution were added thereto and it was put on ice. Cells were scraped with a scraper, moved to an effendorf tube, centrifuged at 4° C. at 14000 rpm for 40 seconds to remove supernatant, and 100 μl of 0.25 M Tris-Cl (pH 7.5) was added to mix with the cells. A process for freezing under liquid nitrogen and immediately melting at 37° C. was repeated 5 times. The pulverized cells were centrifuged at 4° C. at 12000 rpm for 10 minutes and supernatant was moved to a new tube to analyze it.

30 μl of cell extracts, 3 μl of 100× magnesium solution (0.1 M MgCl$_2$, 4.5 M β-mercaptoethanol), 66 μl of 1×ONPG (4 ml/ml in 0.1 M sodium phosphate (pH 7.5)), and 201 μl of 0.1 M sodium phosphate (pH 7.5) were mixed well, and reacted at 37° C. until the color changed to yellow. After adding 500 μl of 1 M Na$_2$CO$_3$, absorbance was measured at 420 nm.

The protein amount in solution was measured by the bicinchoninic acid (BCA) method (Smith et al., 1985, *Anal. Biochem.* 150, 76-85).

Figure 4:
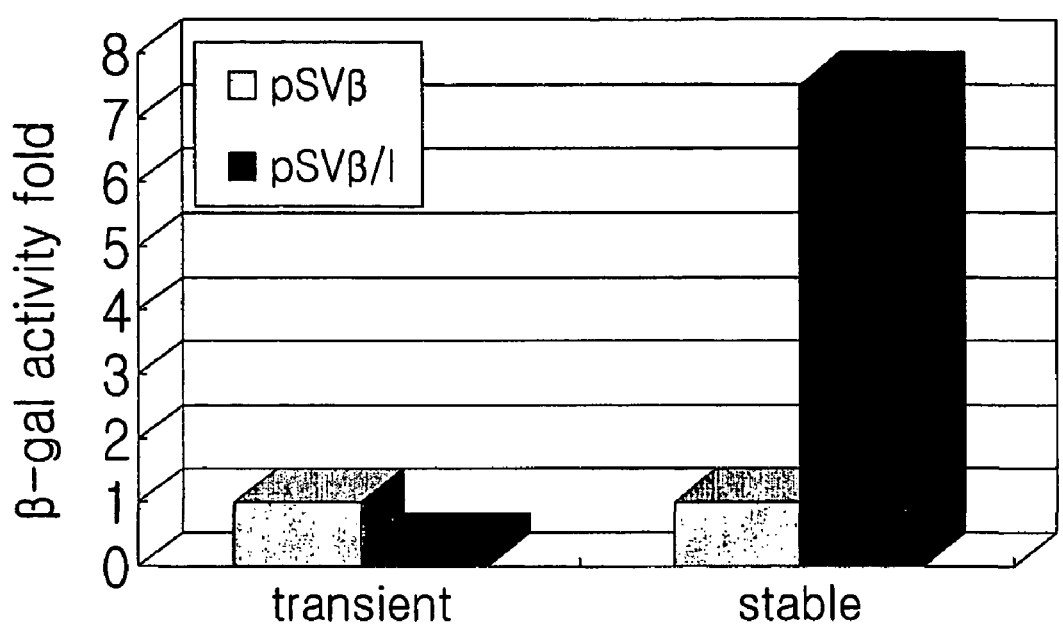
FIG. 4 shows β-gal expression frequency and expression amount in a G418 selection medium.
Figure 5:
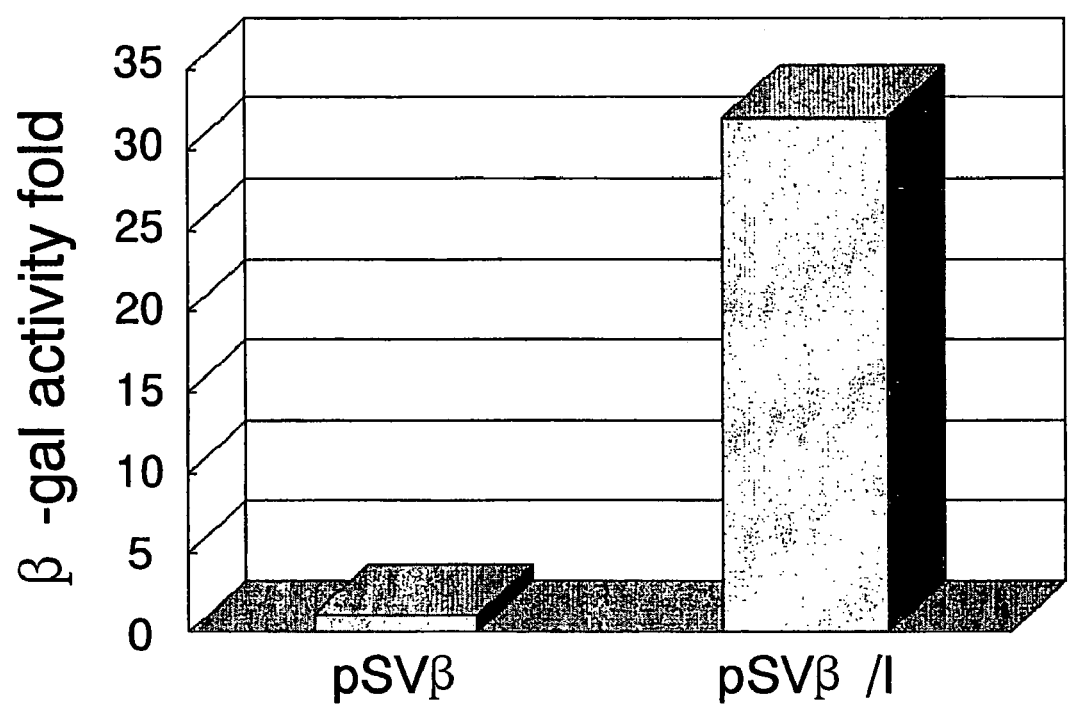
FIG. 5 shows β-gal expression frequency and expression amount in a DHFR selection medium.

FIG. 4 is a graph measuring β-gal activity of DG44/pSVβ or DG44/pSVβ/I selected with the Neo selection maker. FIG. 5 is a graph measuring β-gal activity of DG44/pSVβ or DG44/pSVβ/I selected with the DHFR selection maker.

When the MAR factor existed in the expression vector, β-gal activities increased 7.5 times (FIG. 4) and 32 times (FIG. 5), respectively. This indicates that, considering the frequency of positive cells, expressed β-gal protein activity per positive cell substantially increased.

EXAMPLE 6

Measurement of β-gal Expression of pCMVβ and pCMVβ/I

Each of pCMBβ and pCMVβ/I was transfected into DG44 by the same method as in Example 5, and number of β-gal positive cell lines and activities were measured.

Figure 6:
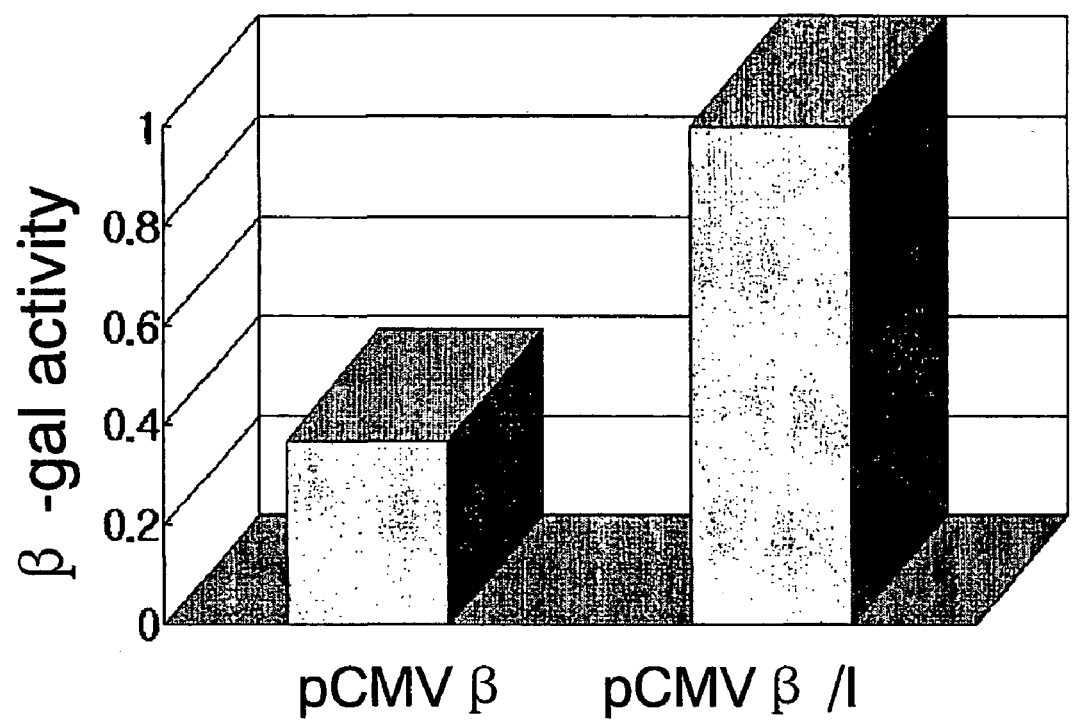
FIG. 6 shows β-gal expression frequency and expression amount in the presence of a CMV promoter.

FIG. 6 is a graph showing β-gal activities of DG44/pCMVβ and DG44/pCMVβ/I, and Table 8 shows the number of β-gal positive cells of DG44/pCMVβ and DG44/pCMVβ/I.

TABLE 8

| | Total Cell number | Positive Cell number | Negative Cell number | Positive Cell Frequency (%) |
|---|---|---|---|---|
| DG44/pCMVβ | 180 | 147 | 33 | 18.33 |
| DG44/pCMVβ/I | 326 | 79 | 247 | 75.77 |

The MAR factor increased frequency of positive cell lines from 18.33% to 75.77% even under a CMV promoter, and it increased the total number of colonies by about 1.8 times and the number of positive colonies by about 7.5 times. Therefore, it is suggested that the effects of interferon β MAR factor are not limited to the SV40 promoter, and that the MAR factor of the present invention can be used in various promoter including SV40, CMV promoter, and other promoters.

EXAMPLE 7

Construction pPGM-1 Vector

Figure 7:
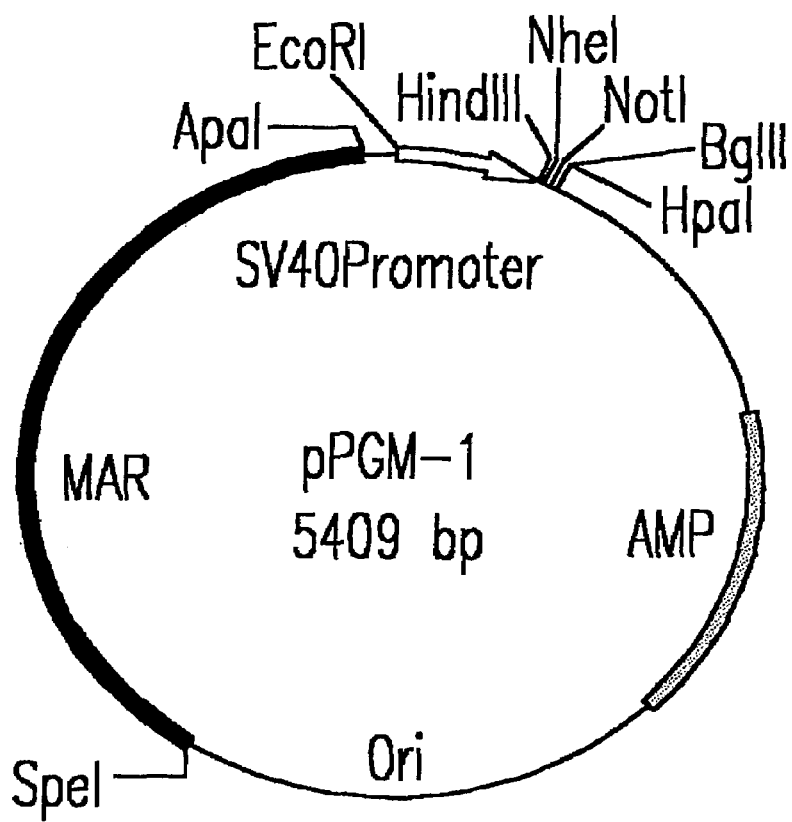
FIG. 7 shows the structure of the pPGM-1 expression vector of the present invention.

A β-gal site was deleted from a pSVβ/I vector and multiple cloning sites (MCS) were insertedtroduced to construct a pPGM-1 vector with the genetic map of FIG. 7.

A HindIII-BamHI fragment including a β-gal gene was removed from a pSVβ/I vector, and 160 bp of a HindIII/BamHI fragment of pMSG (KCCM 10202) was inserted. The pPGM-1 vector was deposited with the Korean Culture Collection of Microorganisms and assigned deposit No. KCCM 10232.

EXAMPLE 8

Construction of pPGM-2 Vector

A pPGM-1 vector was inserted with multiple cloning sites to construct a pPGM-2 vector.

A HindIII-BamHI fragment of a pSVβ vector was substituted with a pMSG (KCCM 10202) derived corresponding fragment, and the vector was opened with an EcoRI enzyme to integrate an interferon MAR factor. It was treated with NheI and XhoI enzymes and a fragment including multiple cloning sites and a T7 promoter was ligated. The fragment was prepared using a PCR primer (Sequence No. 20 and Sequence No. 21) comprising AvrII and SalI restriction site.

FIG. 8 shows the map of the pPGM-2 vector and base sequence of multiple cloning sites, and the vector was deposited with the Korean Culture Collection of Microorganisms and assigned deposit No. KCCM 10338.

EXAMPLE 9

Construction of pPGM-3 Vector

A HindIII-BamHI fragment of pSVβ-1 vector was substituted with a pMSG (KCCM 10202) derived corresponding fragment. The vector was digested with EcoRI and NheI to delete a promoter and substitute it with a CMV promoter, and it was opened with an EcoRI enzyme to ligate an interferon MAR factor. The structure of the constructed pPGM-3 vector is shown in FIG. 9, and its deposit No. is KCCM 10339.

EXAMPLE 10

Production of Recombinant Protein Using pPGM-1 Vector

The pPGM-1 vector was digested with NheI and XhoI enzymes and integrated genes were ligated. The genes were cDNA encoding human growth hormone (Gene Bank #: E01424) or human interferon β (Gene Bank #: V00534).

Figure 10:
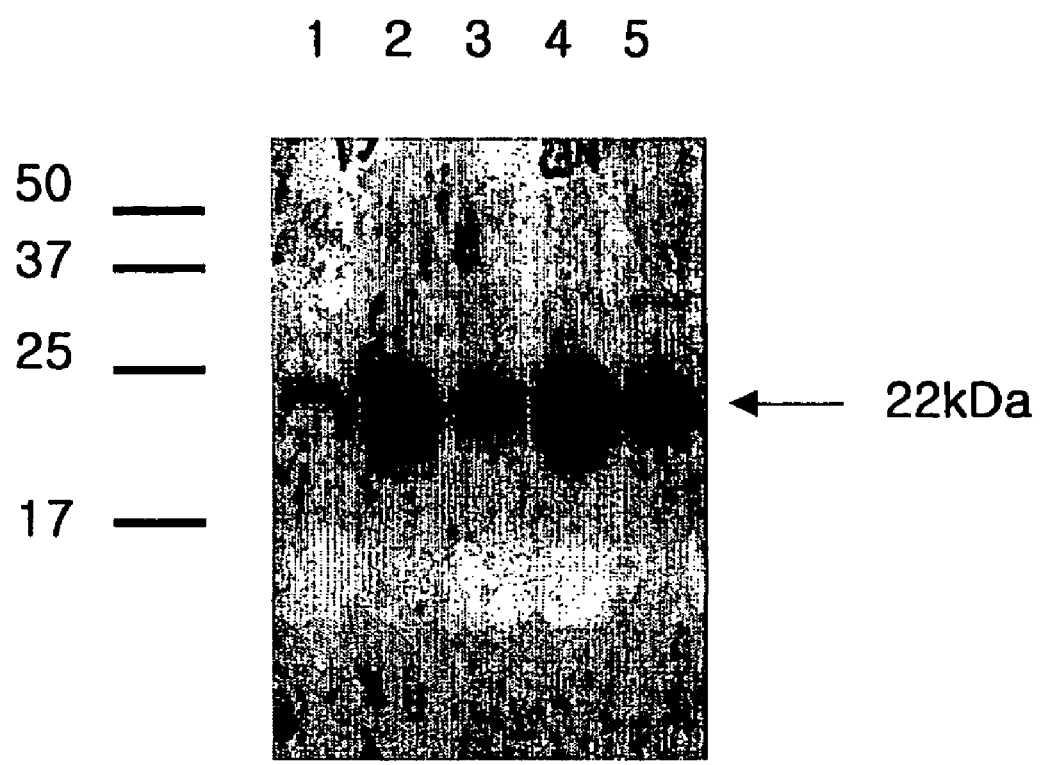
FIG. 10 shows results of analyzing expression titer of a human growth hormone expression cell line prepared using pPGM-1, by Western Blot.
Figure 11:
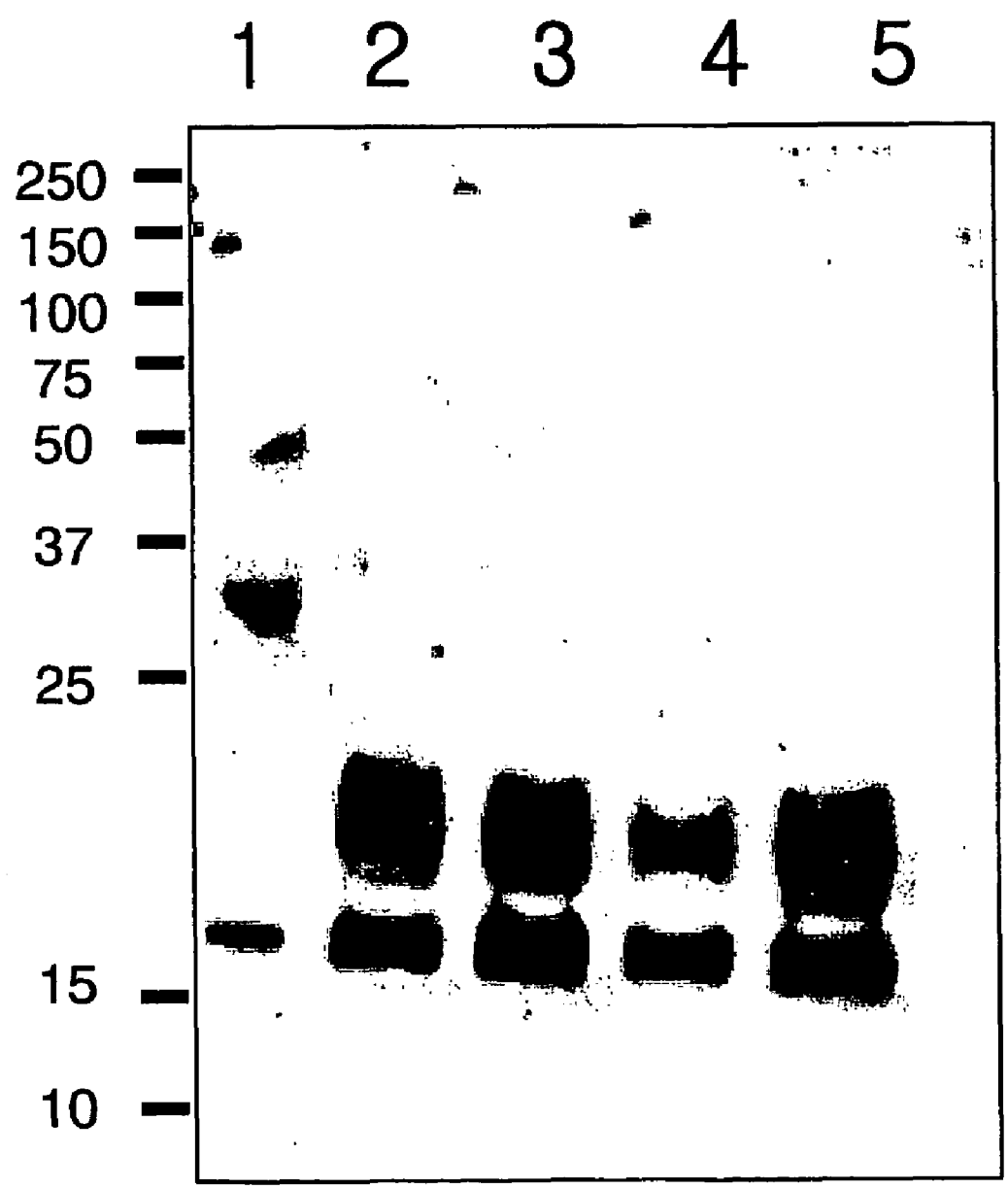
FIG. 11 shows results of analyzing expression titer of an interferon β expression cell line prepared using pPGM-1, by Western Blot.

The constructed expression vector was transfected into CHO DG44 cells and a high expression transfected cell line was selected while increasing the concentration of MTX added to a medium. Expression titer was measured by Western Blot, as shown in FIGS. 10 and 11.

$1.08 \times 10^5$ cells were put in a 12-well plate and cultured for 48 hours, and the medium was pooled to carry out Western Blot. Lane 1 is 25 ng of positive control protein, and lanes 2-5 are culture solutions derived from different colonies selected. The expression rate for human growth hormones was measured at about 20 μg/ml/day, and the expression rate for interferon β was approximately 15 μg/ml/day.

---

What is claimed is:

1. A mammalian expression vector comprising:
   (a) a nuclear matrix attachment region of an interferon β gene;
   (b) a promoter; and
   (c) a transcription terminator,
   wherein the mammalian expression vector increases expression of a transgene in a CHO (Chinese Hamster Ovary) cell, and wherein the mammalian expression vector is pPGM-1 KCCM 10232.

2. A mammalian expression vector comprising:
   (a) a nuclear matrix attachment region of an interferon β gene;
   (b) a promoter; and
   (c) a transcription terminator,
   wherein the mammalian expression vector increases expression of a transgene in a CHO (Chinese Hamster Ovary) cell, and wherein the mammalian expression vector is pPGM-2 KCCM 10338.

3. A mammalian expression vector comprising:
   (a) a nuclear matrix attachment region of an interferon β gene;
   (b) a promoter; and
   (c) a transcription terminator,
   wherein, the mammalian expression vector increases expression of a transgene in a CHO (Chinese Hamster Ovary) cell, and wherein the mammalian expression vector is pPGM-3 KCCM 10339.

4. A mammalian expression vector comprising:
   (a) a nuclear matrix attachment region of an interferon β gene;
   (b) a promoter; and
   (c) a transcription terminator,
   wherein the mammalian expression vector increases expression of a transgene in a CHO (Chinese Hamster Ovary) cell, the CHO (Chinese Hamster Ovary) cell transfected with the mammalian expression vector in which the expression vector comprises a transgene, and wherein the mammalian expression vector is selected from a group consisting of pPGM-1 (KCCM 10232), pPGM-2 (KCCM 10338), and pPGM-3 (KCCM 10339).

5. A method of producing recombinant protein comprising:
   introducing a transgene into a mammalian expression vector comprising:
   (a) a nuclear matrix attachment region of an interferon β gene;
   (b) a promoter; and
   (c) a transcription tenninator,
   wherein, the mammalian expression vector increases expression of a transgene in a CHO (Chinese Hamster Ovary) cell, and
   transfecting CHO (Chinese Hamster Ovary) cells with the expression vector in order to express protein from the transgene, and wherein the mammalian expression vector is selected from a group consisting of pPGM-1 (KCCM 10232), pPGM-2 (KCCM 10338), and pPGM-3 (KCCM 10339).

* * * * *

SEQUENCE LISTING

```
<160> NUMBER OF SEQ ID NOS: 21

<210> SEQ ID NO 1
<211> LENGTH: 5409
<212> TYPE: DNA
<213> ORGANISM: Artificial Sequence
<220> FEATURE:
<223> OTHER INFORMATION: pPGM-1 vector
<220> FEATURE:
<221> NAME/KEY: promoter
<222> LOCATION: (1)..(419)
<223> OTHER INFORMATION: SV40 virus
<220> FEATURE:
<221> NAME/KEY: gene
<222> LOCATION: (449)..(584)
<223> OTHER INFORMATION: small T antigen of SV40 virus
<220> FEATURE:
<221> NAME/KEY: gene
<222> LOCATION: (1194)..(2054)
<223> OTHER INFORMATION: beta-lactamase
<220> FEATURE:
<221> NAME/KEY: gene
<222> LOCATION: (3225)..(5397)
<223> OTHER INFORMATION: interferon beta MAR

<400> SEQUENCE: 1
```

```
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc     120
cagcaggcag aagtatgcaa agcatgcatc tcaattagtc agcaaccagg tgtggaaagt     180
ccccaggctc cccagcaggc agaagtatgc aaagcatgca tctcaattag tcagcaacca     240
tagtcccgcc cctaactccg cccatcccgc cctaactcc gcccagttcc gcccattctc      300
cgccccatgg ctgactaatt ttttttattt atgcagaggc cgaggccgcc tcggcctctg     360
agctattcca gaagtagtga ggaggctttt tggaggcct aggcttttgc aaaaagcttg      420
ctagcggccg cagatctgtt aactcgagaa cttgtttatt gcagcttata atggttacaa     480
ataaagcaat agcatcacaa atttcacaaa taaagcattt ttttcactgc attctagttg     540
tggtttgtcc aaactcatca atgtatctta tcatgtctgg atcggcatgc aagctggcac     600
tggccgtcgt tttacaacgt cgtgactggg aaaaccctgg cgttacccaa cttaatcgcc     660
ttgcagcaca tccccctttc gccagctggc gtaatagcga agaggcccgc accgatcgcc     720
cttcccaaca gttgcgcagc ctgaatggcg aatggcgcct gatgcggtat tttctcctta     780
cgcatctgtg cggtatttca caccgcatat ggtgcactct cagtacaatc tgctctgatg     840
ccgcatagtt aagccagccc cgacacccgc caacacccgc tgacgcgccc tgacgggctt     900
gtctgctccc ggcatccgct tacagacaag ctgtgaccgt ctccgggagc tgcatgtgtc     960
agaggttttc accgtcatca ccgaaacgcg cgagacgaaa gggcctcgtg atacgcctat    1020
ttttataggt taatgtcatg ataataatgg tttcttagac gtcaggtggc acttttcggg    1080
gaaatgtgcg cggaacccct atttgtttat ttttctaaat acattcaaat atgtatccgc    1140
tcatgagaca ataaccctga taaatgcttc aataatattg aaaaaggaag agtatgagta    1200
ttcaacattt ccgtgtcgcc cttattccct ttttttgcggc attttgcctt cctgttttg    1260 ctcacccaga aacgctggtg aaagtaaaag atgctgaaga tcagttgggt gcacgagtgg    1320
gttacatcga actggatctc aacagcggta agatccttga gttttcgc cccgaagaac      1380 gttttccaat gatgagcact tttaaagttc tgctatgtgg cgcggtatta cccgtattg     1440 acgccgggca agagcaactc ggtcgccgca tacactattc tcagaatgac ttggttgagt    1500
actcaccagt cacagaaaag catcttacgg atggcatgac agtaagagaa ttatgcagtg    1560
ctgccataac catgagtgat aacactgcgg ccaacttact tctgacaacg atcggaggac    1620
cgaaggagct aaccgctttt ttgcacaaca tgggggatca tgtaactcgc cttgatcgtt    1680
gggaaccgga gctgaatgaa gccataccaa acgacgagcg tgacaccacg atgcctgtag    1740
caatggcaac aacgttgcgc aaactattaa ctggcgaact acttactcta gcttcccggc    1800
aacaattaat agactggatg gaggcggata agttgcagg accacttctg cgctcggccc     1860
ttccggctgg ctggtttatt gctgataaat ctggagccgg tgagcgtggg tctcgcggta    1920
tcattgcagc actggggcca gatggtaagc cctcccgtat cgtagttatc tacacgacgg    1980
ggagtcaggc aactatggat gaacgaaata gacagatcgc tgagataggt gcctcactga    2040
ttaagcattg gtaactgtca gaccaagttt actcatatat actttagatt gatttaaaac    2100
ttcattttta atttaaaagg atctaggtga agatcctttt tgataatctc atgaccaaaa    2160
tcccttaacg tgagttttcg ttccactgag cgtcagaccc cgtagaaaag atcaaaggat    2220
cttcttgaga tccttttttt ctgcgcgtaa tctgctgctt gcaaacaaaa aaaccaccgc    2280
taccagcggt ggtttgtttg ccggatcaag agctaccaac tctttttccg aaggtaactg    2340
```

-continued

```
gcttcagcag agcgcagata ccaaatactg ttcttctagt gtagccgtag ttaggccacc    2400
acttcaagaa ctctgtagca ccgcctacat acctcgctct gctaatcctg ttaccagtgg    2460
ctgctgccag tggcgataag tcgtgtctta ccgggttgga ctcaagacga tagttaccgg    2520
ataaggcgca gcggtcgggc tgaacggggg gttcgtgcac acagcccagc ttggagcgaa    2580
cgacctacac cgaactgaga tacctacagc gtgagctatg agaaagcgcc acgcttcccg    2640
aagggagaaa ggcggacagg tatccggtaa gcggcagggt cggaacagga gagcgcacga    2700
gggagcttcc aggggaaac gcctggtatc tttatagtcc tgtcgggttt cgccacctct    2760
gacttgagcg tcgattttg tgatgctcgt cagggggcg gagcctatgg aaaaacgcca    2820
gcaacgcggc cttttacgg ttcctggcct tttgctggcc ttttgctcac atgttctttc    2880
ctgcgttatc ccctgattct gtggataacc gtattaccgc ctttgagtga gctgataccg    2940
ctcgccgcag ccgaacgacc gagcgcagcg agtcagtgag cgaggaagcg gaagagcgcc    3000
caatacgcaa accgcctctc cccgcgcgtt ggccgattca ttaatgcagc tggcacgaca    3060
ggtttcccga ctggaaagcg ggcagtgagc gcaacgcaat taatgtgagt tagctcactc    3120
attaggcacc ccaggcttta cactttatgc ttccggctcg tatgttgtgt ggaattgtga    3180
gcggataaca atttcacaca ggaaacagct atgacatgat tacgaattca gcaaggtcgc    3240
cacgcacaag atcaatatta acaatcagtc atctctcttt agcaataaaa aggtgaaaaa    3300
ttacatttta aaaatgacac catagacgat gtatgaaaat aatctacttg gaaataaatc    3360
taggcaaaga agtgcaagac tgttacccag aaaacttaca aattgtaaat gagaggttag    3420
tgaagattta aatgaatgaa gatctaaata aacttataaa ttgtgagaga aattaatgaa    3480
tgtctaagtt aatgcagaaa cggagagaca tactatattc atgaactaaa agacttaata    3540
ttgtgaaggt atactttctt ttcacataaa tttgtagtca atatgttcac cccaaaaaag    3600
ctgtttgtta acttgtcaac ctcatttcaa aatgtatata gaaagcccaa agacaataac    3660
aaaaatattc ttgtagaaca aaatgggaaa gaatgttcca ctaaatatca agatttagag    3720
caaagcatga gatgtgtggg gatagacagt gaggctgata aaatagagta gagctcagaa    3780
acagacccat tgatatatgt aagtgaccta tgaaaaaaat atggcatttt acaatgggaa    3840
aatgatgatc ttttctttt ttagaaaaac agggaaatat atttatatgt aaaaaataaa    3900
agggaaccca tatgtcatac catacacaca aaaaaattcc agtgaattat aagtctaaat    3960
ggagaaggca aaactttaaa tcttttagaa aataatatag aagcatgcca tcatgacttc    4020
agtgtagaga aaaatttctt atgactcaaa gtcctaacca caagaaaag attgttaatt    4080 agattgcatg aatattaaga cttattttta aaattaaaaa accattaaga aaagtcaggc    4140
catagaatga cagaaaatat ttgcaacacc ccagtaaaga gaattgtaat atgcagatta    4200 taaaagaag tcttacaaat cagtaaaaaa taaaactaga caaaaatttg aacagatgaa    4260
agagaaactc taaataatca ttacacatga gaaactcaat ctcagaaatc agagaactat    4320
cattgcatat acactaaatt agagaaatat taaaaggcta agtaacatct gtggcaatat    4380
tgatggtata taaccttgat atgatgtgat gagaacagta ctttaccca tgggcttcct    4440 ccccaaaccc ttaccccagt ataaatcatg acaaatatac tttaaaaacc attaccctat    4500
atctaaccga tactcctcaa aactgtcaag gtcatcaaaa ataagaaaag tctgaggaac    4560
tgtcaaaact aagaggaacc caaggagaca tgagaattat atgtaatgtg gcattctgaa    4620
tgagatccca gaacagaaaa agaacagtag ctaaaaaact aatgaaatat aaataaagtt    4680
tgaactttag ttttttttaa aaaagagtag cattaacacg gcaaagtcat tttcatattt    4740
```

-continued

```
ttcttgaaca ttaagtacaa gtctataatt aaaaattttt taaatgtagt ctggaacatt    4800
gccagaaaca gaagtacagc agctatctgt gctgtcgcct aactatccat agctgattgg    4860
tctaaaatga gatacatcaa cgctcctcca tgttttttgt tttcttttta aatgaaaaac    4920
tttatttttt aagaggagtt tcaggttcat agcaaaattg agaggaaggt acattcaagc    4980
tgaggaagtt ttcctctatt cctagtttac tgagagattg catcatgaat gggtgttaaa    5040
ttttgtcaaa tgcttttct gtgtctatca atatgaccgt gtgattttct tctttaacct    5100
gttgatggga caaattacgt taattgattt tcaaacgttg aaccacccct acatatctgg    5160
aataaattct acttggttgt ggtgtatatt ttttgataca ttcttggatt cttttttgcta   5220 atattttgtt gaaatgtttt gtatctttgt tcatgagaga tattggtctg ttgttttctt    5280
ttcttgtaat gtcattttct agttccggta ttaaggtaat gctggcctag ttgaatgatt    5340
taggaagtat tccctctgct tctgtcttct gaaagagatt gtagaaagtt gatacaaaag    5400
ccgaattcg                                                            5409

<210> SEQ ID NO 2
<211> LENGTH: 5546
<212> TYPE: DNA
<213> ORGANISM: Artificial Sequence
<220> FEATURE:
<223> OTHER INFORMATION: pPGM-2 vector
<220> FEATURE:
<221> NAME/KEY: promoter
<222> LOCATION: (1)..(419)
<223> OTHER INFORMATION: SV40 virus
<220> FEATURE:
<221> NAME/KEY: primer_bind
<222> LOCATION: (426)..(445)
<223> OTHER INFORMATION: T7 promoter
<220> FEATURE:
<221> NAME/KEY: gene
<222> LOCATION: (1331)..(2191)
<223> OTHER INFORMATION: beta-lactamase gene
<220> FEATURE:
<221> NAME/KEY: gene
<222> LOCATION: (3361)..(5534)
<223> OTHER INFORMATION: Interferon beta MAR elemen

<400> SEQUENCE: 2
gcgcagcacc atggcctgaa ataacctctg aaagaggaac ttggttaggt accttctgag      60
gcggaaagaa ccagctgtgg aatgtgtgtc agttagggtg tggaaagtcc ccaggctccc    120
cagcaggcag aagtatgcaa agcatgcatc tcaattagtc agcaaccagg tgtggaaagt    180
ccccaggctc cccagcaggc agaagtatgc aaagcatgca tctcaattag tcagcaacca    240
tagtcccgcc cctaactccg cccatcccgc cctaactcc gcccagttcc gcccattctc      300
cgccccatgg ctgactaatt ttttttattt atgcagaggc cgaggccgcc tcggcctctg    360
agctattcca gaagtagtga ggaggctttt ttggaggcct aggcttttgc aaaaagcttg    420
ctaggtaata cgactcacta tagggagacc caagctggct agcgtttaaa cttaagcttg    480
gtaccgagct cggatccact agtccagtgt ggtggaattc tgcagatatc cagcacagtg    540
gcggccgctc gagtctagag ggcccgttta acacgcgtg tcgagaactt gtttattgca    600
gcttataatg gttacaaata aagcaatagc atcacaaatt tcacaaataa agcatttttt    660
tcactgcatt ctagttgtgg tttgtccaaa ctcatcaatg tatcttatca tgtctggatc    720
ggcatgcaag ctggcactgg ccgtcgtttt acaacgtcgt gactgggaaa accctggcgt    780
tacccaactt aatcgccttg cagcacatcc ccctttcgcc agctggcgta atagcgaaga    840
```

-continued

```
ggcccgcacc gatcgccctt cccaacagtt gcgcagcctg aatggcgaat ggcgcctgat      900
gcggtatttt ctccttacgc atctgtgcgg tatttcacac cgcatatggt gcactctcag      960
tacaatctgc tctgatgccg catagttaag ccagccccga cacccgccaa cacccgctga     1020
cgcgccctga cgggcttgtc tgctcccggc atccgcttac agacaagctg tgaccgtctc     1080
cgggagctgc atgtgtcaga ggttttcacc gtcatcaccg aaacgcgcga gacgaaaggg     1140
cctcgtgata cgcctatttt tataggttaa tgtcatgata ataatggttt cttagacgtc     1200
aggtggcact tttcggggaa atgtgcgcgg aaccccctatt tgtttatttt tctaaataca    1260
ttcaaatatg tatccgctca tgagacaata accctgataa atgcttcaat aatattgaaa     1320
aaggaagagt atgagtattc aacatttccg tgtcgccctt attccctttt ttgcggcatt     1380
ttgccttcct gtttttgctc acccagaaac gctggtgaaa gtaaaagatg ctgaagatca     1440
gttgggtgca cgagtgggtt acatcgaact ggatctcaac agcggtaaga tccttgagag     1500
ttttcgcccc gaagaacgtt ttccaatgat gagcactttt aaagttctgc tatgtggcgc     1560
ggtattatcc cgtattgacg ccgggcaaga gcaactcggt cgccgcatac actattctca     1620
gaatgacttg gttgagtact caccagtcac agaaaagcat cttacggatg gcatgacagt     1680
aagagaatta tgcagtgctg ccataaccat gagtgataac actgcggcca acttacttct     1740
gacaacgatc ggaggaccga aggagctaac cgcttttttg cacaacatgg ggatcatgt     1800
aactcgcctt gatcgttggg aaccggagct gaatgaagcc ataccaaacg acgagcgtga     1860
caccacgatg cctgtagcaa tggcaacaac gttgcgcaaa ctattaactg gcgaactact     1920
tactctagct tcccggcaac aattaataga ctggatggag gcggataaag ttgcaggacc     1980
acttctgcgc tcggcccttc cggctggctg gtttattgct gataaatctg gagccggtga     2040
gcgtgggtct cgcggtatca ttgcagcact ggggccagat ggtaagccct cccgtatcgt     2100
agttatctac acgacgggga gtcaggcaac tatggatgaa cgaaatagac agatcgctga     2160
gataggtgcc tcactgatta agcattggta actgtcagac caagtttact catatatact     2220
ttagattgat ttaaaacttc atttttaatt taaaaggatc taggtgaaga tcctttttga     2280
taatctcatg accaaaatcc cttaacgtga gttttcgttc cactgagcgt cagaccccgt     2340
agaaaagatc aaaggatctt cttgagatcc tttttttctg cgcgtaatct gctgcttgca     2400
aacaaaaaaa ccaccgctac cagcggtggt ttgtttgccg gatcaagagc taccaactct     2460
ttttccgaag gtaactggct tcagcagagc gcagatacca aatactgttc ttctagtgta    2520
gccgtagtta ggccaccact tcaagaactc tgtagcaccg cctacatacc tcgctctgct     2580
aatcctgtta ccagtggctg ctgccagtgg cgataagtcg tgtcttaccg ggttggactc     2640
aagacgatag ttaccggata aggcgcagcg gtcgggctga acggggggtt cgtgcacaca     2700
gcccagcttg gagcgaacga cctacaccga actgagatac ctacagcgtg agctatgaga     2760
aagcgccacg cttcccgaag ggagaaaggc ggacaggtat ccggtaagcg gcagggtcgg     2820
aacaggagag cgcacgaggg agcttccagg gggaaacgcc tggtatcttt atagtcctgt     2880
cgggtttcgc cacctctgac ttgagcgtcg attttgtga tgctcgtcag ggggcggag      2940
cctatggaaa aacgccagca acgcggcctt tttacggttc ctggcctttt gctggccttt     3000
tgctcacatg ttctttcctg cgttatcccc tgattctgtg ataaccgta ttaccgcctt      3060
tgagtgagct gataccgctc gccgcagccg aacgaccgag cgcagcgagt cagtgagcga     3120
ggaagcggaa gagcgcccaa tacgcaaacc gcctctcccc gcgcgttggc cgattcatta     3180
atgcagctgg cacgacaggt ttcccgactg gaaagcgggc agtgagcgca acgcaattaa     3240
```

-continued

```
tgtgagttag ctcactcatt aggcacccca ggctttacac tttatgcttc cggctcgtat    3300
gttgtgtgga attgtgagcg gataacaatt tcacacagga aacagctatg acatgattac    3360
gaattcagca aggtcgccac gcacaagatc aatattaaca atcagtcatc tctctttagc    3420
aataaaaagg tgaaaaatta cattttaaaa atgacaccat agacgatgta tgaaaataat    3480
ctacttggaa ataaatctag gcaaagaagt gcaagactgt tacccagaaa acttacaaat    3540
tgtaaatgag aggttagtga agatttaaat gaatgaagat ctaaataaac ttataaattg    3600
tgagagaaat taatgaatgt ctaagttaat gcagaaacgg agagacatac tatattcatg    3660
aactaaaaga cttaatattg tgaaggtata cttcttttc ataaattt gtagtcaata    3720 tgttcacccc aaaaagctg tttgttaact tgtcaacctc atttcaaaat gtatatagaa    3780
agcccaaaga caataacaaa atatattcttg tagaacaaaa tgggaaagaa tgttccacta    3840
aatatcaaga tttagagcaa agcatgagat gtgtggggat agacagtgag gctgataaaa    3900
tagagtagag ctcagaaaca gacccattga tatatgtaag tgacctatga aaaaaatatg    3960
gcattttaca atgggaaaat gatgatcttt tctttttta gaaaacagg gaaatatatt    4020 tatatgtaaa aaataaaagg gaacccatat gtcataccat acacacaaaa aaattccagt    4080
gaattataag tctaaatgga gaaggcaaaa ctttaaatct tttagaaaat aatatagaag    4140
catgccatca tgacttcagt gtagagaaaa atttcttatg actcaaagtc ctaaccacaa    4200
agaaaagatt gttaattaga ttgcatgaat attaagactt attttaaaa ttaaaaaacc    4260 attaagaaaa gtcaggccat agaatgacag aaaatatttg caacaccca gtaaagagaa    4320 ttgtaatatg cagattataa aaagaagtct tacaaatcag taaaaaataa aactagacaa    4380
aaatttgaac agatgaaaga gaaactcaa ataatcatta cacatgagaa actcaatctc    4440
agaaatcaga gaactatcat tgcatataca ctaaattaga gaaatattaa aaggctaagt    4500
aacatctgtg gcaatattga tggtatataa ccttgatatg atgtgatgag aacagtactt    4560
taccccatgg gcttcctccc caaaccctta ccccagtata aatcatgaca aatatacttt    4620
aaaaaccatt accctatatc taaccagtac tcctcaaaac tgtcaaggtc atcaaaaata    4680
agaaaagtct gaggaactgt caaaactaag aggaacccaa ggagacatga gaattatatg    4740
taatgtggca ttctgaatga gatcccagaa cagaaaaaga acagtagcta aaaaactaat    4800
gaaatataaa taagtttga actttagttt tttttaaaaa agagtagcat taacacggca    4860
aagtcatttt catattttc ttgaacatta agtacaagtc tataattaaa aatttttaa    4920 atgtagtctg gaacattgcc agaaacagaa gtacagcagc tatctgtgct gtcgcctaac    4980
tatccatagc tgattggtct aaaatgagat acatcaacgc tcctccatgt tttttgtttt    5040 cttttaaat gaaaaacttt atttttaag aggagtttca ggttcatagc aaaattgaga    5100
ggaaggtaca ttcaagctga ggaagttttc ctctattcct agtttactga gagattgcat    5160
catgaatggg tgttaaattt tgtcaaatgc tttttctgtg tctatcaata tgaccgtgtg    5220
attttcttct ttaacctgtt gatgggacaa attacgttaa ttgattttca aacgttgaac    5280 caccccttaca tatctggaat aaattctact tggttgtggt gtatatttt tgatacattc    5340 ttggattctt tttgctaata ttttgttgaa aatgtttgta tctttgttca tgagagatat    5400
tggtctgttg ttttctttc ttgtaatgtc attttctagt tccggtatta aggtaatgct    5460
ggcctagttg aatgatttag gaagtattcc ctctgcttct gtcttctgaa agagattgta    5520
gaaagttgat acaaaagccg aattcg                                         5546
```

<210> SEQ ID NO 3
<211> LENGTH: 5601
<212> TYPE: DNA
<213> ORGANISM: Artificial Sequence
<220> FEATURE:
<223> OTHER INFORMATION: pPGM-3 vector
<220> FEATURE:
<221> NAME/KEY: promoter
<222> LOCATION: (1)..(611)
<223> OTHER INFORMATION: CMV promoter
<220> FEATURE:
<221> NAME/KEY: gene
<222> LOCATION: (1386)..(2246)
<223> OTHER INFORMATION: beta-lactamase gene
<220> FEATURE:
<221> NAME/KEY: gene
<222> LOCATION: (3417)..(5589)
<223> OTHER INFORMATION: Interferon beta MAR element

<400> SEQUENCE: 3

| | | | | | |
|---|---|---|---|---|---|
| gaattcacta | gtgattaggg | cccgttgaca | ttgattattg | actagttatt | aatagtaatc     60 |
| aattacgggg | tcattagttc | atagcccata | tatggagttc | cgcgttacat | aacttacggt    120 |
| aaatggcccg | cctggctgac | cgcccaacga | cccccgccca | ttgacgtcaa | taatgacgta    180 |
| tgttcccata | gtaacgccaa | tagggacttt | ccattgacgt | caatgggtgg | agtatttacg    240 |
| gtaaactgcc | cacttggcag | tacatcaagt | gtatcatatg | ccaagtacgc | cccctattga    300 |
| cgtcaatgac | ggtaaatggc | ccgcctggca | ttatgcccag | tacatgacct | tatgggactt    360 |
| tcctacttgg | cagtacatct | acgtattagt | catcgctatt | accatggtga | tgcggttttg    420 |
| gcagtacatc | aatgggcgtg | gatagcggtt | tgactcacgg | ggatttccaa | gtctccaccc    480 |
| cattgacgtc | aatgggagtt | tgttttggca | ccaaaatcaa | cgggactttc | caaaatgtcg    540 |
| taacaactcc | gccccattga | cgcaaatggg | cggtaggcgt | gtacggtggg | aggtctatat    600 |
| aagcagagct | cgctagcggc | cgcagatctg | ttaactcgag | aacttgttta | ttgcagctta    660 |
| taatggttac | aaataaagca | atagcatcac | aaatttcaca | aataaagcat | ttttttcact    720 |
| gcattctagt | tgtggtttgt | ccaaactcat | caatgtatct | tatcatgtct | ggatcggcat    780 |
| gcaagctggc | actggccgtc | gttttacaac | gtcgtgactg | ggaaaaccct | ggcgttaccc    840 |
| aacttaatcg | ccttgcagca | catcccccTt | tcgccagctg | gcgtaatagc | gaagaggccc    900 |
| gcaccgatcg | cccttcccaa | cagttgcgca | gcctgaatgg | cgaatggcgc | ctgatgcggt    960 |
| attttctcct | tacgcatctg | tgcggtattt | cacaccgcat | atggtgcact | ctcagtacaa   1020 |
| tctgctctga | tgccgcatag | ttaagccagc | cccgacaccc | gccaacaccc | gctgacgcgc   1080 |
| cctgacgggc | ttgtctgctc | ccggcatccg | cttacagaca | agctgtgacc | gtctccggga   1140 |
| gctgcatgtg | tcagaggttt | tcaccgtcat | caccgaaacg | cgcgagacga | aagggcctcg   1200 |
| tgatacgcct | atttttatag | gttaatgtca | tgataataat | ggtttcttag | acgtcaggtg   1260 |
| gcacttttcg | gggaaatgtg | cgcggaaccc | ctatttgttt | atttttctaa | atacattcaa   1320 |
| atatgtatcc | gctcatgaga | caataaccct | gataaatgct | tcaataatat | tgaaaaagga   1380 |
| agagtatgag | tattcaacat | ttccgtgtcg | cccttattcc | cttttttgcg | gcattttgcc   1440 |
| ttcctgtttt | tgctcaccca | gaaacgctgg | tgaaagtaaa | agatgctgaa | gatcagttgg   1500 |
| gtgcacgagt | gggttacatc | gaactggatc | tcaacagcgg | taagatcctt | gagagttttc   1560 |
| gccccgaaga | acgttttcca | atgatgagca | cttttaaagt | tctgctatgt | ggcgcggtat   1620 |
| tatcccgtat | tgacgccggg | caagagcaac | tcggtcgccg | catacactat | tctcagaatg   1680 |
| acttggttga | gtactcacca | gtcacagaaa | agcatcttac | ggatggcatg | acagtaagag   1740 |

```
aattatgcag tgctgccata accatgagtg ataacactgc ggccaactta cttctgacaa   1800
cgatcggagg accgaaggag ctaaccgctt ttttgcacaa catgggggat catgtaactc   1860
gccttgatcg ttgggaaccg gagctgaatg aagccatacc aaacgacgag cgtgacacca   1920
cgatgcctgt agcaatggca acaacgttgc gcaaactatt aactggcgaa ctacttactc   1980
tagcttcccg gcaacaatta atagactgga tggaggcgga taaagttgca ggaccacttc   2040
tgcgctcggc ccttccggct ggctggttta ttgctgataa atctggagcc ggtgagcgtg   2100
ggtctcgcgg tatcattgca gcactgggc cagatggtaa gccctcccgt atcgtagtta   2160
tctacacgac ggggagtcag gcaactatgg atgaacgaaa tagacagatc gctgagatag   2220
gtgcctcact gattaagcat tggtaactgt cagaccaagt ttactcatat atactttaga   2280
ttgatttaaa acttcatttt taatttaaaa ggatctaggt gaagatcctt tttgataatc   2340
tcatgaccaa aatcccttaa cgtgagtttt cgttccactg agcgtcagac cccgtagaaa   2400
agatcaaagg atcttcttga gatcctttt ttctgcgcgt aatctgctgc ttgcaaacaa   2460
aaaaaccacc gctaccagcg gtggtttgtt tgccggatca agagctacca actcttttc   2520
cgaaggtaac tggcttcagc agagcgcaga taccaaatac tgttcttcta gtgtagccgt   2580
agttaggcca ccacttcaag aactctgtag caccgcctac atacctcgct ctgctaatcc   2640
tgttaccagt ggctgctgcc agtggcgata agtcgtgtct taccgggttg gactcaagac   2700
gatagttacc ggataaggcg cagcggtcgg gctgaacggg gggttcgtgc acacagccca   2760
gcttggagcg aacgacctac accgaactga gatacctaca gcgtgagcta tgagaaagcg   2820
ccacgcttcc cgaagggaga aaggcggaca ggtatccggt aagcggcagg gtcggaacag   2880
gagagcgcac gagggagctt ccaggggga acgcctggta tctttatagt cctgtcgggt   2940
ttcgccacct ctgacttgag cgtcgatttt tgtgatgctc gtcaggggg cggagcctat   3000
ggaaaaacgc cagcaacgcg gccttttac ggttcctggc cttttgctgg ccttttgctc   3060
acatgttctt tcctgcgtta tcccctgatt ctgtggataa ccgtattacc gcctttgagt   3120
gagctgatac cgctcgccgc agccgaacga ccgagcgcag cgagtcagtg agcgaggaag   3180
cggaagagcg cccaatacgc aaaccgcctc tccccgcgcg ttggccgatt cattaatgca   3240
gctggcacga caggtttccc gactggaaag cgggcagtga gcgcaacgca attaatgtga   3300
gttagctcac tcattaggca ccccaggctt tacactttat gcttccggct cgtatgttgt   3360
gtggaattgt gagcggataa caatttcaca caggaaacag ctatgacatg attacgaatt   3420
cagcaaggtc gccacgcaca agatcaatat taacaatcag tcatctctct ttagcaataa   3480
aaaggtgaaa aattacattt taaaaatgac accatagacg atgtatgaaa ataatctact   3540
tggaaataaa tctaggcaaa gaagtgcaag actgttaccc agaaaactta caaattgtaa   3600
atgagaggtt agtgaagatt taaatgaatg aagatctaaa taaacttata aattgtgaga   3660
gaaattaatg aatgtctaag ttaatgcaga aacggagaga catactatat tcatgaacta   3720
aaagacttaa tattgtgaag gtatactttc ttttcacata aatttgtagt caatatgttc   3780
accccaaaaa agctgtttgt taacttgtca acctcatttc aaaatgtata tagaaagccc   3840
aaagacaata acaaaaatat tcttgtagaa caaaatggga agaatgttc cactaaatat   3900
caagatttag agcaaagcat gagatgtgtg gggatagaca gtgaggctga taaaatagag   3960
tagagctcag aaacagaccc attgatatat gtaagtgacc tatgaaaaaa atatggcatt   4020
ttacaatggg aaaatgatga tcttttttctt ttttagaaaa acaggaaat atatttatat   4080
```

-continued

```
gtaaaaaata aaagggaacc catatgtcat accatacaca caaaaaaatt ccagtgaatt    4140
ataagtctaa atggagaagg caaaactttta aatcttttag aaaataatat agaagcatgc    4200
catcatgact tcagtgtaga gaaaaatttc ttatgactca aagtcctaac cacaaagaaa    4260
agattgttaa ttagattgca tgaatattaa gacttatttt taaaattaaa aaaccattaa    4320
gaaaagtcag gccatagaat gacagaaaat atttgcaaca ccccagtaaa gagaattgta    4380
atatgcagat tataaaaaga agtcttacaa atcagtaaaa aataaaacta gacaaaaatt    4440
tgaacagatg aaagagaaac tctaaataat cattacacat gagaaactca atctcagaaa    4500
tcagagaact atcattgcat atacactaaa ttagagaaat attaaaaggc taagtaacat    4560
ctgtggcaat attgatggta tataaccttg atatgatgtg atgagaacag tactttaccc    4620
catgggcttc ctccccaaac ccttacccca gtataaatca tgacaaatat actttaaaaa    4680
ccattaccct atatctaacc agtactcctc aaaactgtca aggtcatcaa aaataagaaa    4740
agtctgagga actgtcaaaa ctaagaggaa cccaaggaga catgagaatt atatgtaatg    4800
tggcattctg aatgagatcc cagaacagaa aaagaacagt agctaaaaaa ctaatgaaat    4860
ataaataaag tttgaacttt agtttttttt aaaaagagt agcattaaca cggcaaagtc    4920
attttcatat ttttcttgaa cattaagtac aagtctataa ttaaaaattt tttaaatgta    4980
gtctggaaca ttgccagaaa cagaagtaca gcagctatct gtgctgtcgc ctaactatcc    5040
atagctgatt ggtctaaaat gagatacatc aacgctcctc catgtttttt gttttctttt    5100
taaatgaaaa acttttatttt ttaagaggag tttcaggttc atagcaaaat tgagaggaag    5160
gtacattcaa gctgaggaag ttttcctcta ttcctagttt actgagagat tgcatcatga    5220
atgggtgtta aattttgtca aatgcttttt ctgtgtctat caatatgacc gtgtgatttt    5280 cttcttttaac ctgttgatgg gacaaattac gttaattgat tttcaaacgt tgaaccaccc    5340
ttacatatct ggaataaatt ctacttggtt gtggtgtata tttttttgata cattcttgga    5400 ttctttttgc taatattttg ttgaaaatgt ttgtatcttt gttcatgaga gatattggtc    5460
tgttgttttc ttttcttgta atgtcatttt ctagttccgg tattaaggta atgctggcct    5520
agttgaatga tttaggaagt attccctctg cttctgtctt ctgaaagaga ttgtagaaag    5580
ttgatacaaa agccgaattc g                                              5601
```

<210> SEQ ID NO 4
<211> LENGTH: 20
<212> TYPE: DNA
<213> ORGANISM: Artificial Sequence
<220> FEATURE:
<223> OTHER INFORMATION: primer for MAR of chicken lysozyme A
<400> SEQUENCE: 4

```
ggatccataa tataactgta                                                  20
```

<210> SEQ ID NO 5
<211> LENGTH: 20
<212> TYPE: DNA
<213> ORGANISM: Artificial Sequence
<220> FEATURE:
<223> OTHER INFORMATION: primer for MAR of chicken lysozyme A
<400> SEQUENCE: 5

```
aagcttaaaa gattgaagca                                                  20
```

<210> SEQ ID NO 6
<211> LENGTH: 20

```
<212> TYPE: DNA
<213> ORGANISM: Artificial Sequence
<220> FEATURE:
<223> OTHER INFORMATION: primer for chicken phi alpha-globin 5' MAR

<400> SEQUENCE: 6
aagcttttaa ccaacaaaaa                                              20

<210> SEQ ID NO 7
<211> LENGTH: 20
<212> TYPE: DNA
<213> ORGANISM: Artificial Sequence
<220> FEATURE:
<223> OTHER INFORMATION: primer for chicken phi alpha-globin 5' MAR

<400> SEQUENCE: 7
ctgcagacct aacctgtcac                                              20

<210> SEQ ID NO 8
<211> LENGTH: 20
<212> TYPE: DNA
<213> ORGANISM: Artificial Sequence
<220> FEATURE:
<223> OTHER INFORMATION: primer for CHO DHFR intron MAR

<400> SEQUENCE: 8
tatacgtgaa tagttttttct                                             20

<210> SEQ ID NO 9
<211> LENGTH: 20
<212> TYPE: DNA
<213> ORGANISM: Artificial Sequence
<220> FEATURE:
<223> OTHER INFORMATION: primer for CHO DHFR intron MAR

<400> SEQUENCE: 9
gagttggaac tgagaagttc                                              20

<210> SEQ ID NO 10
<211> LENGTH: 20
<212> TYPE: DNA
<213> ORGANISM: Artificial Sequence
<220> FEATURE:
<223> OTHER INFORMATION: primer for human HPRT intron MAR

<400> SEQUENCE: 10
aagcttggtc aagaatgctg                                              20

<210> SEQ ID NO 11
<211> LENGTH: 20
<212> TYPE: DNA
<213> ORGANISM: Artificial Sequence
<220> FEATURE:
<223> OTHER INFORMATION: primer for human HPRT intron MAR

<400> SEQUENCE: 11
gctgggcgtg gtggtgcctg                                              20

<210> SEQ ID NO 12
<211> LENGTH: 20
<212> TYPE: DNA
<213> ORGANISM: Artificial Sequence
<220> FEATURE:
<223> OTHER INFORMATION: primer for human CSP-B gene flanking SAR
      element

<400> SEQUENCE: 12
```

```
ggatcccatt ctccttgatg                                                    20

<210> SEQ ID NO 13
<211> LENGTH: 20
<212> TYPE: DNA
<213> ORGANISM: Artificial Sequence
<220> FEATURE:
<223> OTHER INFORMATION: primer for human CSP-B gene flanking SAR
      element

<400> SEQUENCE: 13
gaattcaaac aactcaatag                                                    20

<210> SEQ ID NO 14
<211> LENGTH: 20
<212> TYPE: DNA
<213> ORGANISM: Artificial Sequence
<220> FEATURE:
<223> OTHER INFORMATION: primer for human interferon-beta gene flanking
      SAR element

<400> SEQUENCE: 14
gaattcagca aggtcgccac                                                    20

<210> SEQ ID NO 15
<211> LENGTH: 20
<212> TYPE: DNA
<213> ORGANISM: Artificial Sequence
<220> FEATURE:
<223> OTHER INFORMATION: primer for human interferon-beta gene flanking
      SAR element

<400> SEQUENCE: 15
ttgtatcaac tttctacaat                                                    20

<210> SEQ ID NO 16
<211> LENGTH: 31
<212> TYPE: DNA
<213> ORGANISM: Artificial Sequence
<220> FEATURE:
<223> OTHER INFORMATION: sense primer for constructing pSV-beta-gal
      /ver1 vector

<400> SEQUENCE: 16
gcactagtcc cgggcccatg attacgaatt c                                       31

<210> SEQ ID NO 17
<211> LENGTH: 25
<212> TYPE: DNA
<213> ORGANISM: Artificial Sequence
<220> FEATURE:
<223> OTHER INFORMATION: sense primer for constructing pSV-beta-gal
      /ver1 vector

<400> SEQUENCE: 17
gtgccagctt gcatgcctgc aggtc                                              25

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
agggcccgtt gacattgatt attg                                               24
```

```
<210> SEQ ID NO 19
<211> LENGTH: 36
<212> TYPE: DNA
<213> ORGANISM: Artificial Sequence
<220> FEATURE:
<223> OTHER INFORMATION: primer

<400> SEQUENCE: 19
aagcttgcta gcgagctctg cttatataga cctccc                              36

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
cctaggtaat acgactcact ataggg                                         26

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
gtcgacacgc gtgtttaaac gggccctcta g                                   31
```